US006245743B1

(12) United States Patent
Marlowe et al.

(10) Patent No.: US 6,245,743 B1
(45) Date of Patent: *Jun. 12, 2001

(54) INHIBITORS OF FACTOR XA

(75) Inventors: Charles K. Marlowe; Robert M. Scarborough, both of Belmont; Alan M. Laibelman, San Mateo; Uma Sinha, San Francisco; Bing-Yan Zhu, Belmont, all of CA (US)

(73) Assignee: COR Therapeutics, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/077,001

(22) PCT Filed: Jun. 5, 1996

(86) PCT No.: PCT/US96/09285

§ 371 Date: May 15, 1998

§ 102(e) Date: May 15, 1998

(87) PCT Pub. No.: WO96/40743

PCT Pub. Date: Dec. 19, 1996

(51) Int. Cl.$^7$ ............... A61K 38/00; C07K 7/00; C07K 5/00
(52) U.S. Cl. ............... 514/18; 514/19; 530/331
(58) Field of Search ............... 514/18, 19; 530/331

(56) References Cited

U.S. PATENT DOCUMENTS

| 3,867,364 | 2/1975 | Umezawa | 424/177 |
|---|---|---|---|
| 4,316,889 | 2/1982 | Bajusz | 424/197 |
| 4,399,065 | 8/1983 | Bajusz | 260/112.5 |
| 4,478,745 | 10/1984 | Bajusz | 260/112.5 |
| 4,588,587 | 5/1986 | Gasic | 424/95 |
| 4,593,018 | 6/1986 | Austen | 514/16 |
| 4,797,472 | 1/1989 | Gustaffson et al. | 530/331 |
| 5,153,176 | 10/1992 | Abe | 514/18 |
| 5,371,072 | 12/1994 | Webb | 514/18 |
| 5,380,713 | 1/1995 | Balasubramanian | 514/18 |
| 5,496,927 | * 3/1996 | Kolb | 530/328 |
| 5,523,308 | 6/1996 | Costanzo | 514/317 |
| 5,721,214 | * 2/1998 | Marlowe | 514/19 |

FOREIGN PATENT DOCUMENTS

| 0 045 665 A1 | 10/1982 | (EP) . |
|---|---|---|
| 0 195 212 A3 | 9/1986 | (EP) . |
| 0275 101 | * 7/1988 | (EP) . |
| 0 275 101 A3 | 7/1988 | (EP) . |
| 0 352 903 A2 | 1/1990 | (EP) . |
| 0 364 344 A3 | 4/1990 | (EP) . |
| 0 410 411 A2 | 1/1991 | (EP) . |
| 0 417 721 A2 | 3/1991 | (EP) . |
| 0 479 489 A2 | 2/1992 | (EP) . |
| 0 504 064 A1 | 9/1992 | (EP) . |
| 0 643 073 A1 | 3/1995 | (EP) . |
| 648780 | 4/1995 | (EP) . |
| 6327488 | 11/1994 | (JP) . |
| 93/14779 | 5/1993 | (WO) . |
| 93/15756 | 8/1993 | (WO) . |
| 94/08941 | 4/1994 | (WO) . |
| 94/13693 | 6/1994 | (WO) . |
| 94/25051 | 10/1994 | (WO) . |
| 95/09634 | 4/1995 | (WO) . |
| 96/19493 | 6/1996 | (WO) . |

OTHER PUBLICATIONS

Almquist, R.G., et al., J. Med. Chem., vol. 23:1392–1398(–COCH$_2$) (1980).

Angelastro, et al., J. Med. Chem., vol. 33:11–13 (1990).

Bajusz, S. et la., "Design and Synthesis of peptide inhibitors of blood coagulations," Folia Haematol., vol. 109(1):16–21 (1982).

Blankenship, D.T. et al., "Amino Acid Sequence of Ghilanten: Anti–coagulant–antimetastatic Principle of the South American Leech, *Haementeria ghilianii*," Biochem. Biophys. Res. Commun., vol. 166:1384–1389 (1990).

Brankamp, R.G. et al., "Ghilantens: Anticoagulants, Antimetastatic Proteins from the South American Leech *Haementeria ghilianii*," J. Lab. Clin. Med., vol. 115:89–97 (199.

Bundgard, H., *Design of Produrgs*, pp. 7–9. 21–24. Elsevier, Amsterdam 1985.

CA:97:39405 (1982), Szelke et al.

Cappello, M. et al., "Ancylostoma Factor Xa Inhibitor: Partial Purification and its Identification as a Major Hookworm–derived Anticoagulant In Vitro," J. Infect. Dis., Vo 167:1474–1477 (1993).

Chemical Abstracts, vol. 124(23):1296 (1996) XP002017940, Okonogi K. et al., "Preparation of amino acid and peptide N–heterocyclylcarbonylalkylamides as thrombin inhibitors, 124:317893a,".

Claeson, G., "Synthetic Peptides and Peptidomimetics as Substrates and Inhibitors of Thrombin and Other Proteases in the Blood Coagulation System," Blood Coag. Fibrinol, vol. 5:411–436 (1994).

Condra, C. et al., "Isolation and Structural Characterization of a Potent Inhibitor of Coagulation Factor Xa from the Leech *Haementeria ghilianii*," Thromb, Haemost., vol. 61:437–441 (1989).

Cox A.C., "Coagulation Factor X Inhibitor From the Hundred–pace Snake *Deinagkistrodon acutus*, venom," Toxicon, vol. 31:1445–1457 (1993).

Davie, E.J., et al., The Coagulation Cascade: Initiation, Maintenance and Regulation, Biochemistry, vol. 30:10363–10370 (1991).

Etingen, O.R., et al., Cell., vol. 61:657 (1990).

Furie, B., et al., Cell, vol. 53:505 (1988).

(List continued on next page.)

*Primary Examiner*—F. T. Moezie
(74) *Attorney, Agent, or Firm*—Cooley Godward LLP

(57) ABSTRACT

Novel compounds, their salts and compositions related thereto having activity against mammalian factor Xa are disclosed. The compounds are useful in vitro or in vivo for preventing or treating coagulation disorders.

11 Claims, No Drawings

OTHER PUBLICATIONS

Girard, T.J. et al., "Comparison of the Anticoagulant and Antithrombotic Effects of Synthetic Thrombin and Factor Xa Inhibitor," Nature, vol. 338:518–520 (1989).

Hann, M.M., *J. Chem Soc Perkin Trans I*, pp. 307–314 (1982).

Hauptmann, J. et al., "Comparison of the Anticoagulant and Antithrombotic Effects of Synthetic Thrombin and Factor Xa Inhibitord," Thromb. Haemost, vol. 63:220–223 (1990).

Hitomi, Y. et al., "Inhibitory Effect of New Synthetic Protease Inhibitor (FUT–175) on the Coagulation System," Haemostatis, vol. 15:164–168 (1985).

Holladay, M.W. et al., Tetrahedron Lett., vol. 24:4401–4404 (1983).

Hollenbach, S. et al., Thromb. Haemost., vol. 71:357–362 (1994).

Hoover, R.J. et al., Cell, vol. 14:423 (1978).

Hruby, V.J., Life Sci, vol. 31:189–199 (1982).

Hudson D. et al., Int. J. Pept. Prot. Res., vol. 14:177–185 (1979).

Jacobs, J.W. et al., "Isolation and Characterization of a Coagulation Factor Xa Inhibitor form Black Fly Salivary Glands," Thromb. Haemost., vol. 64:235–238 (1990).

Jennings–White C. et al., Tetrahedron Lett., vol. 23:2533 (1982).

Kam, C.M. et al., "Mechanism Based Isocoumarin Inhibitors for Trypsin and Blood Coagulation Serine Proteases: New Anticoagulants," Biochemistry, vol. 27:2547–2557 (1988).

Kettner, C. et al., J. Biol. Chem., vol. 265:18289–18297 (1990).

Medhi, G. et al., Biochem. Biophys. Res. Commun., vol. 166:595–600 (1990).

Morley, J.S., Trends Pharm. Sci., pp. 463–468 (1980).

Nagahara, T. et al., "Dibasic (Amidinoaryl)propanoic Acid Derivatives as Novel Blood Coagulation Factor Xa Inhibitors," J. Med. Chem., vol. 37:1200–1207 (1994).

Nutt, E. et al., "The Amino Acid Sequence of Antistasis, a Potent Inhibitor of Factor Xa Reveals a Repeated Internal Structure," J. Biol. Chem., vol. 263:10162–10167 (1988).

Ohta et al., "Interaction of Antistasin–related Peptides with Factor Xa: Identification of a Core Inhibitory Sequence," Thrombosis and Haemstasis, vol. 72(6):825–830 (1994).

Seymour J.L. et al., "Ecotin is a Potent Anticogagulant and Reversible Tight Binding Inhibitor of Factor Xa," Biochemistry, vol. 33:3949–3958 (1994).

Silverman, R.B., *The Organic Chemistry of Drug Design and Drug Action*, pp. 352–401, Academic Press, San Diego, Ca (1992).

Sinha, U. et al., Thromb. Res., vol. 75:427–436 (1994).

Skiles, J.W. et al., J. Med. Chem., vol. 35:641–662 (1992).

Spatola, A.F., in "Chemistry and Biochemistry of Amino Acids, Peptides and Proteins," B. Weinstein, eds., Marcel Dekker, New York, pp. 267–335 (1983).

Spatola, A.F. et al., Life Sci, vol. 38:1243–1249 (1986).

Sturzebecher, J. et al., "Synthetic Inhibitors of Bovine Factor Xa and Thrombin. Comparison of Their Anticoagulant Efficiency," Thromb. Res., vol. 54:245–252 (1989).

Tapparelli et al., J. Biol. Chem., vol. 268:4734–4741 (1993).

Tidwell, R.R. et al., "Strategies for Anticoagulation with Synthetic Protease Inhibitors Xa Inhibitors Versus Thrombin Inhibitors," Thromb. Res., vol. 19:339–349 (1980).

Turner, A.D. et al., "p–Amidino Esters as Irreversible Inhibitors of Factors IXa and Xa and Thrombin," Biochemistry, vol. 25:4929–4935 (1986).

Waxman, L. et al., "Tick Anticoagulant Peptide (TAP) is a Novel Inhibitor of Blood Coagulation Factor Xa," Science, vol. 248:593–596 (1990).

* cited by examiner

INHIBITORS OF FACTOR XA

FIELD OF THE INVENTION

This invention relates to novel arginine and arginine mimetic-containing compounds which are potent and highly selective inhibitors of isolated factor Xa or when assembled in the prothrombinase complex. In another aspect, the present invention relates to novel peptide and peptide mimetic analogs, their pharmaceutically acceptable salts, and pharmaceutically acceptable compositions thereof which are useful as potent and specific inhibitors of blood coagulation in mammals. In yet another aspect, the invention relates to methods for using these inhibitors as therapeutic agents for disease states in mammals characterized by coagulation disorders.

BACKGROUND OF THE INVENTION

Hemostasis, the control of bleeding, occurs by surgical means, or by the physiological properties of vasoconstriction and coagulation. This invention is particularly concerned with blood coagulation and ways in which it assists in maintaining the integrity of mammalian circulation after injury, inflammation, disease, congenital defect, dysfunction or other disruption. Under normal hemostatic circumstances, the body maintains an acute balance of clot formation and clot removal (fibrinolysis). The blood coagulation cascade involves the conversion of a variety of inactive enzymes (zymogens) into active enzymes which ultimately convert the soluble plasma protein fibrinogen into an insoluble matrix of highly cross-linked fibrin, Davie, E. J. et al., "The Coagulation Cascade: Initiation, Maintenance and Regulation", Biochemistry, 30, 10363–10370 (1991). These plasma glycoprotein zymogens include Factor XII, Factor XI, Factor IX, Factor X, Factor VII, and prothrombin. Blood coagulation follows either the intrinsic pathway, where all of the protein components are present in blood, or the extrinsic pathway, where the cell-membrane protein tissue factor plays a critical role. Clot formation occurs when fibrinogen is cleaved by thrombin to form fibrin. Blood clots are composed of activated platelets and fibrin.

Blood platelets which adhere to damaged blood vessels are activated and incorporated into the clot and thus play a major role in the initial formation and stabilization of hemostatic "plugs". In certain diseases of the cardiovascular system, deviations from normal hemostasis push the balance of clot formation and clot dissolution towards life-threatening thrombus formation when thrombi occlude blood flow in coronary vessels (myocardial Infarctions) or limb and pulmonary veins (venous thrombosis). Although platelets and blood coagulation are both involved in thrombus formation, certain components of the coagulation cascade are primarily responsible for the amplification or acceleration of the processes involved in platelet aggregation and fibrin deposition.

Thrombin is a key enzyme in the coagulation cascade as well as in hemostasis. Thrombin plays a central role in thrombosis through its ability to catalyze the conversion of fibrinogen into fibrin and through its potent platelet activation activity. Under normal circumstances, thrombin can also play an anticoagulant role In hemostasis through its ability to convert protein C into activated protein C (aPC) in a thrombomodulin-dependent manner. However, in atherosclerotic arteries these thrombin activities can initiate the formation of a thrombus, which is a major factor in pathogenesis of vasoocdusive conditions such as myocardial infarction, unstable angina, nonhemorrhagic stroke and reocclusion of coronary arteries after angioplasty or thrombolytic therapy. Thrombin is also a potent inducer of smooth muscle cell proliferation and may therefore be involved in a variety of proliferative responses such as restenosis after angioplasty and graft induced atherosclerosis. In addition, thrombin is chemotactic for leukocytes and may therefore play a role in inflammation. (Hoover, R. J., et al. Cell, 14, 423 (1978); Etingin, O. R., et al., Cell, 61, 657 (1990). These observations indicate that inhibition of thrombin formation or inhibition of thrombin itself may be effective in preventing or treating thrombosis, limiting restenosis and controlling inflammation.

Direct or indirect inhibition of thrombin activity has been the focus of a variety of recent anticoagulant strategies as reviewed by Claeson, G., "Synthetic Peptides and Peptidomimetics as Substrates and Inhibitors of Thrombin and Other Proteases in the Blood Coagulation System", Blood Coag. Fibrinol. 5, 411–436 (1994). Several classes of anticoagulants currently used in the clinic directly or indirectly affect thrombin (i.e. heparins, low-molecular weight heparins, heparin-like compounds and coumarins).

The formation of thrombin is the result of the proteolytic cleavage of its precursor prothrombin at the Arg-Thr linkage at positions 271–272 and the Arg-lle linkage at positions 320–321. This activation is catalyzed by the prothrombinase complex, which is assembled on the membrane surfaces of platelets, monocytes, and endothelial cells. The complex consists of Factor Xa (a serine protease), Factor Va (a cofactor), calcium ions and the acidic phospholipid surface. Factor Xa is the activated form of its precursor, Factor X, which is secreted by the liver as a 56 kd precursor and is converted to the active form, Factor Xa, in both the extrinsic and intrinsic blood coagulation pathways. Factor X is a member of the calcium ion binding, gamma carboxyglutamyl (Gla)-containing, vitamin K dependent, blood coagulation glycoprotein family, which also includes Factors VII and IX, prothrombin, protein C and protein S (Furie, B., et al., Cell, 53, 505 (1988)). The activity of Factor Xa in effecting the conversion of prothrombin to thrombin is dependent on its inclusion in the prothrombinase complex.

The prothrombinase complex converts the zymogen prothrombin into the active procoagulant thrombin. It is therefore understood that Factor Xa catalyzes the next-to-last step in the blood coagulation cascade, namely the formation of the serine protease thrombin. In turn, thrombin then acts to cleave soluble fibrinogen in the plasma to form insoluble fibrin.

The location of the prothrombinase complex at the convergence of the intrinsic and extrinsic coagulation pathways, and the resulting significant amplification of thrombin generation (several hundred-thousand fold faster in effecting the conversion of prothrombin to thrombin than Factor Xa in soluble form) mediated by the complex at a limited number of targeted catalytic units present at vascular lesion sites, suggests that inhibition of thrombin generation is a desirable method to block uncontrolled procoagulant activity. It has been suggested that compounds which selectively inhibit factor Xa may be useful as in vitro diagnostic agents, or for therapeutic administration in certain thrombotic disorders, see e.g., WO 94/13893. Unlike thrombin, which acts on a variety of protein substrates as well as at a specific receptor, factor Xa appears to have a single physiologic substrate, namely prothrombin.

Plasma contains an endogenous inhibitor of both the factor Vlla-tissue factor (TF) complex and factor Xa called tissue factor pathway inhibitor (TFPI). TFPI is a Kunitz-type protease inhibitor with three tandem Kunitz domains. TFPI inhibits the TF/fVIIa complex in a two-step mechanism which includes the initial interaction of the second Kunitz domain of TFPI with the active site of factor Xa, thereby inhibiting the proteolytic activity of factor Xa. The second step involves the inhibition of the TF/fVIIa complex by formation of a quaternary complex TF/fVIIa/TFPI/fXa as described by Girard, T. J. et al., "Functional Significance of the Kunitz-type Inhibitory Domains of Lipoprotein-associated Coagulation Inhibitor", Nature, 338, 518–520 (1989).

Polypeptides derived from hematophagous organisms have been reported which are highly potent and specific inhibitors of factor Xa. U.S. Pat. No. 4,588,587 describes anticoagulant activity in the saliva of the Mexican leech, *Haementeria officinalis*. A principal component of this saliva was shown to be the polypeptide factor Xa inhibitor, antistasin (ATS), by Nutt, E. et al., "The Amino Acid Sequence of Antistasin, a Potent Inhibitor of Factor Xa Reveals a Repeated Internal Structure", J. Biol. Chem., 263, 10162–10167 (1988).

Another potent and highly specific inhibitor of Factor Xa, called tick anticoagulant peptide CAP), has been isolated from the whole body extract of the soft tick *Omithidoros moubata*, as reported by Waxman, L., et al., "Tick Anticoagulant Peptide (TAP) is a Novel Inhibitor of Blood Coagulation Factor Xa" Science, 248, 593–596 (1990).

Other polypeptide type inhibitors of factor Xa have been reported including the following: Condra, C. et al., "Isolation and Structural Characterization of a Potent Inhibitor of Coagulation Factor Xa from the Leech *Haementeria ghilianii*", Thromb. Haemost., 61, 437–441 (1989); Blankenship, D. T. et al., "Amino Acid Sequence of Ghilanten: Anti-coagulant-antimetastatic Principle of the South American Leech, *Haementeria ghilianii*", Biochem. Biophys. Res. Commun. 166, 1384–1389 (1990); Brankamp, R. G. et al, "Ghilantens: Anticoagulants, Anti-metastatic Proteins from the South American Leech *Haementeria ghilianii*", J. Lab. Clin. Med., 115, 89–97 (1990); Jacobs, J. W. et al., "Isolation and Characterization of a Coagulation Factor Xa Inhibitor from Black Fly Salivary Glands", Thromb. Haemost., 64, 235–238 (1990); Rigbi, M. et al., "Bovine Factor Xa Inhibiting Factor and Pharmaceutical Compositions Containing the Same", European Patent Application, 352,903; Cox, A. C., "Coagulation Factor X Inhibitor From the Hundred-pace Snake *Deinagkistrodon acutus*, venom", Toxicon, 31, 1445–1457 (1993); Cappello, M. et al., "Ancylostoma Factor Xa Inhibitor. Partial Purification and its Identification as a Major Hookworm-derived Anticoagulant In Vitro", J. Infect. Dis., 167, 1474–1477 (1993); Seymour, J. L. et.al., "Ecotin is a Potent Anticoagulant and Reversible Tight-binding Inhibitor of Factor Xa", Biochemistry 33, 3949–3958 (1994).

Factor Xa inhibitory compounds which are not large polypeptide-type inhibitors have also been reported induding: Tidwell, R. R. at al., "Strategies for Anticoagulation With Synthetic Protease Inhibitors. Xa Inhibitors Versus Thrombin Inhibitors", Thromb. Res., 19, 339–349 (1980); Turner, A. D. et al., "p-Amidino Esters as Irreversible Inhibitors of Factor IXa and Xa and Thrombin", Biochemistry, 25, 4929–4935 (1986); Hitorni, Y. et al., "Inhibitory Effect of New Synthetic Protease Inhibitor (FUT-175) on the Coagulation System", Haemostasis, 15, 164–168 (1985); Sturzebecher, J. et al., "Synthetic Inhibitors of Bovine Factor Xa and Thrombin. Comparison of Their Anticoagulant Efficiency", Thromb. Res., 54, 245–252 (1989); Kam, C. M. et al., "Mechanism Based Isocoumarin Inhibitors for Trypsin and Blood Coagulation Serine Proteases: New Anticoagulants", Biochemistry, 27, 2547–2557 (1988); Hauptmann, J. et al., "Comparison of the Anticoagulant and Antithrombotic Effects of Synthetic Thrombin and Factor Xa Inhibitors", Thromb. Haemost, 63, 220–223 (1990); Miyadera, A. et al., Japanese Patent Application JP 6327488; Nagahara, T. et al., "Dibasic (Amidinoaryl) propanoic Acid Derivatives as Novel Blood Coagulation Factor Xa Inhibitors", J. Med. Chem., 37, 1200–1207 (1994); Vlasuk, G. P. et al., "Inhibitors of Thrombosis", WO 93/15756; and Brunck, T. K. et al., "Novel Inhibitors of Factor Xa", WO 94/13693.

A number of inhibitors of trypsin-like enzymes (such as trypsin, enterokinase, thrombin, kallikrein, plasmin, urokinase, plasminogen activators and the like) have been the subject of disclosures. For example, Austen et al., U.S. Pat. No. 4,593,018 describes oligopeptide aldehydes which are specific inhibitors of enterokinase; Abe et al., U.S. Pat. No. 5,153,176 describes tripeptide aldehydes which have inhibitory activity against multiple serine proteases such as plasmin, thrombin, trypsin, kallikrein, factor Xa, urokinase, etc.; Brunck et al., European Publication WO 93/14779 describes substituted tripeptide aldehydes that are specific inhibitors of trypsin; U.S. Pat. No. 4,316,889, U.S. Pat. No. 4,399,065, U.S. Pat. No. 4,478,745 all disclose arginine aldehyde inhibitors of thrombin; Balasubramanian et al., U.S. Pat. No. 5,380,713 describes di and tripeptide aldehydes which are useful for anti-trypsin and anti-thrombin activity; Webb et al., U.S. Pat. No. 5,371,072 describes tripeptide alpha-keto-amide derivatives as inhibitors of thrombosis and thrombin; Gesellchen et al., European Patent Publications 0479489A2 and 0643073 A, describe tripeptide thrombin inhibitors; Veber et al., European Publication WO 94/25051 describes 4-cyclohexylamine derivatives which selectively inhibit thrombin over other trypsin-like enzymes; Tapparelli et al., J. Biol. Chem. 268, 4734–4741 (1993) describe selective peptide boronic acid derivatives as inhibitors of thrombin.

Alternatively, agents which inhibit the vitamin K-dependent carboxylase enzyme, such as coumarin, have been used to treat coagulation disorders.

There exists a need for effective therapeutic agents for the regulation of coagulation disorders, and for the prevention and treatment of thrombus formation and other pathological processes in the vasculature induced by thrombin such as restenosis and inflammation.

SUMMARY OF THE INVENTION

The present invention relates to novel peptide and peptide mimetic analogs, their pharmaceutically acceptable isomers, salts, hydrates, solvates and prodrug derivatives, and pharmaceutically acceptable compositions thereof which have particular biological properties and are useful as potent and specific inhibitors of blood coagulation in mammals. In another aspect, the invention relates to methods of using these inhibitors as diagnostic reagents or as therapeutic agents for disease states in mammals which have coagulation disorders, such as in the treatment or prevention of any thrombotically mediated acute coronary or cerebrovascular syndrome, any thrombotic syndrome occurring in the venous system, any coagulopathy, and any thrombotic complications associated with extracorporeal circulation or instrumentation, and for the inhibition of coagulation in biological samples.

In certain embodiments, this invention relates to novel arginine and arginine mimetic-containing compounds which are potent and highly selective inhibitors of isolated factor Xa when assembled in the prothrombinase complex. These compounds show selectivity for factor Xa versus other proteases of the coagulation cascade (e.g. thrombin, etc.) or the fibrinolytic cascade, and are useful as diagnostic reagents as well as antithrombotic agents.

In preferred embodiments, the present invention provides compounds of the formula:

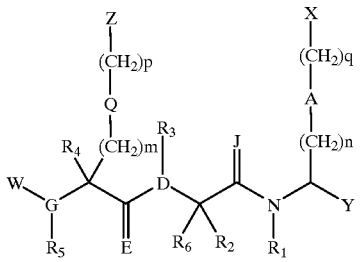

wherein:

m=0,1,2,3,4;

n=0,1,2,3,4;

p=0,1,2,3,4;

q=0,1,2,3,4;

Y=CHO, COCF$_3$, COCF$_2$CF$_3$, COCO$_2$R$_7$, COCONR$_8$R$_9$, B(OR$_{10}$)$_2$; where: R$_7$, R$_8$, R$_9$, R$_{10}$ are the same or different and =H, C$_{1-6}$alkyl, C$_{3-8}$cycloalkyl, arylC$_{1-3}$alkyl, heteroarylC$_{1-3}$alkyl;

A=piperdinyl, pyrrolidinyl, cyclopropyl, cycdobutyl, cyclopentyl, cyclohexyl, phenyl, C$_{3-6}$heteroaryl, or is absent;

R$_1$=H or C$_{1-3}$alkyl;

J=O or H$_2$;

R$_2$=H orC$_{1-3}$alkyl;

D=N, CH, NCH$_2$, NCH$_2$CH$_2$, CHCH$_2$;

R$_3$=H or C$_{1-3}$alkyl;

E=O or H$_2$;

R$_4$=H or CH$_3$;

Q=piperdinyl, pyrrolidinyl, C$_{3-8}$ cycloalkyl, phenyl, substituted phenyl, naphthyl, pyridyl, or is absent;

G=N, CH, or is H;

R$_5$=H or C$_{1-3}$ alkyl, or is absent if G is H;

R$_6$=H or CH$_3$

W=H, arylacyl, heteroarylacyl, arylC$_{1-3}$alkylsulfonyl, arylsulfonyl, substituted arylsulfonyl, arylC$_{1-4}$alkenylsulfonyl, C$_{1-8}$ alkylsulfonyl, heteroarylC$_{1-3}$alkylsulfonyl, heteroarylsulfonyl, aryloxycarbonyl, C$_{1-6}$ alkyloxycarbonyl, arylC$_{1-3}$alkyloxycarbonyl, arylaminocarbonyl, C$_{1-6}$alkylaminocarbonyl, arylC$_{1-3}$alkylaminocarbonyl, HOOC-C$_{0-3}$alkylcarbonyl, or is absent if G is H;

X=H, C$_{1-3}$alkyl, NR'R", NH—C(NR'R")=NH, NH—C(NHR')=NR", S-(NR'R")=NH, S—C(NHR')=NR", C(NR'R")=NH, C(NHR')=NR", or CR'=NR"; where: R',R" are the same or different and =H, C$_{1-6}$alkyl, C$_{1-3}$arylalkyl, aryl or where R'R" forms a cyclic ring containing (CH$_2$)$_p$ where p=2–5, with the proviso that when X is H or C$_{1-3}$alkyl, then A must contain at least one N atom;

Z=H, C$_{1-3}$alkyl, NR'R", NH—C(NR'R")=NH, NH—C(NHR')=NR", S—C(NR'R")=NH, S—C(NHR')=NR", C(NR'R")=NH, C(NHR')=NR", or CR'=NR"; where: R',R" are the same or different and =H, C$_{1-6}$alkyl, C$_{1-3}$arylalkyl, aryl or where R'R" forms a cyclic ring containing (CH$_2$)$_p$ where p=2–5, with the proviso that when Z is H or C$_{1-3}$alkyl, then Q must contain at least one N atom;

and all pharmaceutically acceptable isomers, salts, hydrates, solvates and prodrug derivatives thereof.

In certain aspects of this invention, compounds are provided which are useful as diagnostic reagents. In another aspect, the present invention includes pharmaceutical compositions comprising a pharmaceutically effective amount of the compounds of this invention and a pharmaceutically acceptable carrier. In yet another aspect, the present invention includes methods comprising using the above compounds and pharmaceutical compositions for preventing or treating disease states characterized by disorders of the blood coagulation process In mammals, or for preventing coagulation in stored blood products and samples. Optionally, the methods of this invention comprise administering the pharmaceutical composition in combination with an additional therapeutic agent such as an antithrombotic and/or a thrombolytic agent and/or an anticoagulant.

The preferred compounds also include their pharmaceutically acceptable isomers, hydrates, solvates, salts and prodrug derivatives.

DETAILED DESCRIPTION OF THE INVENTION

Definitions

In accordance with the present invention and as used herein, the following terms are defined with the following meanings, unless explicitly stated otherwise.

The term "alkenyl" refers to a trivalent straight chain or branched chain unsaturated aliphatic radical.

The term "alkyl" refers to saturated aliphatic groups including straight-chain, branched-chain and cyclic groups having the number of carbon atoms specified, or if no number is specified, having up to 12 carbon atoms. The term "cycloalkyl" as used herein refers to a mono-, bi-, or tricyclic aliphatic ring having 3 to 14 carbon atoms and preferably 3 to 7 carbon atoms.

The term "aryl" refers to an unsubstituted or substituted aromatic ring, substituted with one, two or three substituents selected from loweralkoxy, loweralkyl, loweralkylamino, hydroxy, halogen, cyano, hydroxyl, mercapto, nitro, thioalkoxyi carboxaldehyde, carboxyl, carboalkoxy and carboxamide, including but not limited to carbocyclic aryl, heterocyclic aryl, and biaryl groups and the like, all of which may be optionally substituted. Preferred aryl groups include phenyl, halophenyl, loweralkylphenyl, napthyl, biphenyl, phenanthrenyl, naphthacenyl, and aromatic heterocyclics. The term "heteroaryl" as used herein refers to any aryl group, containing from one to four heteroatoms, selected from the group consisting of nitrogen, oxygen and sulfur.

The term "arylalkyl" refers to one, two, or three aryl groups having the number of carbon atoms designated, appended to an alkyl group having the number of carbon atoms designated. Suitable arylalkyl groups include, but are not limited to, benzyl, picolyl, naphthylmethyl, phenethyl, benzyhydryl, trityl, and the like, all of which may be optionally substituted.

The terms "halo" or "halogen" as used herein refer to Cl, Br, F or I substituents.

The term "methylene" refers to —CH$_2$—.

The term "pharmaceutically acceptable salts" includes salts of compounds derived from the combination of a compound and an organic or inorganic acid. These compounds are useful in both free base and salt form. In practice, the use of the salt form amounts to use of the base form; both acid and base addition salts are within the scope of the present invention.

"Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric add, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

"Pharmaceutcally acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium and magnesium salts. Salts derived from pharmaceutically acceptable organic nontoxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicydohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, polyamine resins and the like. Particularly preferred organic nontoxic bases are isopropylamine, diethylamine, ethanolamine, trimethamine, dicyclohexylamine, choline, and caffeine.

"Biological property" for the purposes herein means an in vivo effector or antigenic function or activity that is directly or indirectly performed by a compound of this invention. Effector functions include receptor or ligand binding, any enzyme activity or enzyme modulatory activity, any carrier binding activity, any hormonal activity, any activity in promoting or inhibiting adhesion of cells to an extracellular matrix or cell surface molecules, or any structural role. Antigenic functions include possession of an epitope or antigenic site that is capable of reacting with antibodies raised against it.

The nomenclature used to describe the peptide compounds of the invention follows the conventional practice where the N-terminal amino group is assumed to be to the left and the carboxy group to the right of each amino acid residue in the peptide. In the formulas representing selected specific embodiments of the present invention, the amino- and carboxy-terminal groups, although often not specifically shown, will be understood to be in the form they would assume at physiological pH values, unless otherwise specified. Thus, the N-terminal $H^{+}_{2}$ and C-terminal O— at physiological pH are understood to be present though not necessarily specified and shown, either in specific examples or in generic formulas. Free functional groups on the side chains of the amino acid residues can also be modified by amidation, acylation or other substitution, which can, for example, change the solubility of the compounds without affecting their activity.

In the peptides described herein, each gene-encoded residue, where appropriate, is represented by a single letter designation, corresponding to the trivial name of the amino acid, in accordance with the following conventional list:

| Amino Acid | One-Letter Symbol | Three Letter Symbol |
| --- | --- | --- |
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |

In addition, the following abbreviations are used in this application:

"Ala" refers to L-Alanine.

"D-Ala" refers to D-Alanine.

"β-Ala" refers to 3-aminopropanoic acid.

"Arg" refers to L-Arginine.

"D-Arg" refers to D-Arginine.

"Aib" refers to alpha-aminoisobutyric acid.

"Bn" refers to benzyl.

"t-Boc" refers to t-butoxycarbonyl.

"BOP" refers to benzotriazol-1-yloxy-tris-(dimethylamino)phosphonium hexafluorophosphate.

"Brine" means an aqueous saturated solution of sodium chloride.

"Cbz" refers to benzyloxycarboryl.

"CDI" refers to carbonyldiimidazole.

"DCC" refers to dicydohexylcarbodiimide.

"DCM" refers to dichloromethane.

"DCU" refers to dicyclohexylurea.

"DIEA" refers to diisopropylethylamine.

"DMF" refers to N,N-dimethylformamide.

"EtOAc" refers to ethyl acetate.

"Fm" refers to 9-fluorenylmethyl.

"Gly" refers to glycine.

"HOSu" refers to N-hydroxysuccinimide.

"HATU" refers to O-(7-azabenzotriazol-1-yl)-1,1,3,3-tetramethyluronium hexafluorophosphate.

"HBTU" refers to O-(1H-benzotriazol-1-yl)-1,1,3,3-tetramethyl-uranium hexafluorophosphate.

"HOBt" refers to N-hydroxybenzotriazole.

"IPA" refers to isopropanol.

"D-Lys" refers to D-Lysine.

"MeOH" refers to methanol.

"NaOAc" refers to sodium acetate.

"NMM" refers to 4-methylmorpholine.

"2-NaphthoxyAc" refers to 2-Naphthoxyacetyl.

"Ph" refers to phenyl.

"D-Pro" refers to D-proline.

"Pro" refers to L-proline.
"TEA" refers to triethylamine.
"TFA" refers to trifluoroacetic acid.
"THF" refers to tetrahydrofuran.
"TsOH" refers to p-toluenesulfonic acid.

The amino acids not encoded genetically are abbreviated as described above or have the meanings commonly accepted in the field.

In the compounds of this invention, carbon atoms bonded to four non-identical substituents are asymmetric. Accordingly, the compounds may exist as diastereoisomers, enantiomers or mixtures thereof. The syntheses described herein may employ racemates, enantiomers or diastereomers as starting materials or intermediates. Diastereomeric products resulting from such syntheses may be separated by chromatographic or by crystallization methods, or by other methods known in the art. Likewise, enantiomeric product mixtures may be separated using the same techniques or by other methods known in the art. Each of the asymmetric carbon atoms, when present in the compounds of this invention, may be in one of two configurations (R or S) and both are within the scope of the present invention. In certain specified preferred embodiments of the compounds shown in the present application, the L-form of any amino add residue having an optical isomer is intended unless the D-form is expressly indicated. In the processes described above, the final products may, in some cases, contain a small amount of the products having D or L-form residues, however these products do not affect their therapeutic or diagnostic application.

The compounds of the invention are peptides or compounds which contain amino acid subunits which are partially defined in terms of amino acid residues of designated classes. Amino acid residues can be generally grouped into four major subclasses as follows:

Acidic: The residue has a negative charge due to loss of H ion at physiological pH and the residue is attracted by aqueous solution.

Basic: The residue has a positive charge due to association with H ion at physiological pH and the residue is attracted by aqueous solution.

Neutral/nonpolar: The residues are not charged at physiological pH and the residue is repelled by aqueous solution so as to seek the inner positions in the conformation of a peptide in which it is contained when the peptide is in aqueous medium. These residues are also designated "hydrophobic" herein.

Neutralpolar The residues are not charged at physiological pH, but the residue is attracted by aqueous solution so as to seek the outer positions in the conformation of a peptide in which it is contained when the pepuide is in aqueous It is understood, of course, that in a statistical collection of individual residue molecules some molecules will be charged, and some not, and there will be an attraction for or repulsion from an aqueous medium to a greater or lesser extent. To fit the definition of "charged," a significant percentage (at least approximately 25%) of the individual molecules are charged at physiological pH. The degree of attraction or repulsion required for classification as polar or nonpolar is arbitrary and, therefore, amino acids specifically contemplated by the invention have been classified as one or the other. Most amino acids not specifically named can be classified on the basis of known behavior.

Amino acid residues can be further subdassified as cydic or noncydic, and aromatic or nonaromatic, self-explanatory classifications with respect to the side chain substituent groups of the residues, and as small or large. The residue is considered small if it contains a total of 4 carbon atoms or less, inclusive of the carboxyl carbon. Small residues are, of course, always nonaromatic for naturally occurring protein amino acids.

For the naturally occurring protein amino acids, subclassification according to the foregoing scheme is as follows.
Acidic: Aspartic acid and Glutamic acid;
Basic/noncyclic: Arginine, Lysine;
Basic/cyclic: Histidine;
Neutral/small: Glycine, Serine, Cysteine, Alanine;
Neutral/polar/large/nonaromatic: Threonine, Asparagine, Glutamine;
Neutral/polar/large/aromatic: Tyrosine;
Neutral/nonpolar/large/nonaromatic: Valine, Isoleucine, Leucine, Methionine;
Neutral/nonpolar/large/aromatic: Phenylalanine, and Tryptophan.

The gene-encoded secondary amino acid proline, although technically within the group neutral/nonpolar/large/cyclic and nonaromatic, is a special case due to its known effects on the secondary conformation of peptide chains, and is not, therefore, included in this defined group.

Certain commonly encountered amino acids, which are not encoded by the genetic code, include, for example, beta-alanine (b-Ala), or other omega-amino acids, such as 2,3diamino propionic (2,3-Dap), 2,4-diaminobutyric (2,4-Dab), 4-amino butyric (g-Abu) and so forth, alpha-aminoisobutyric acid (Aib), sarcosine (Sar), ornithine (Om), citrulline (Cit), homoarginine (Har), homolysine (homoLys), n-butylamidinoglycine (Bag), 4-guanidinophenylalanine (4-Gpa), 3-guanidinophenylalanine (3-Gpa), 4-amidinophenylalanine (4-Apa), 3-amidinophenylalanine (3-Apa), 4-aminocyclohexylglycine (4-Acg), 4-aminophenylalanine (4-$NH_2$-Phe), 3-aminophenylalanine (3-$NH_2$-Phe), 3-piperidinylalanine (3-PIA), 4-piperidinylalanine (4-PIA), 3-guanidinopiperidinylalanine (3-GPIA), 4-guanidinopiperidinylalanine (4-GPIA), 3-piperidinylglycine (3-PIG), 4-piperidinylglycine (4-PIG), 3-guanidinopiperidinylglycine (3-GPIG), and 4-guanidinopiperidinylglycine (4-GPIG). These also fall conveniently into particular categories.

Based on the above definitions:
Sar, b-Ala, g-Abu, and Aib are neutral/small;
Orn, Har, homoLys, Bag, 2,3-Dap, 2,4-Dab,4-Gpa, 3-Gpa, 4-Apa, 3-Apa, 4-Acg, 4-$NH_2$-Phe, 3-$NH_2$-Phe, 3-PIA, 4-PIA, 3-GPIA, 4-GPIA, 3-PIG, 4-PIG, 3-GPIG and 4-GPIG are basic;
Cit, is neutral/polar/large/nonaromatic; and
The various omega-amino acids are classified according to size as neutral/nonpolar/small ($\beta$-Ala, i.e., 3-aminopropionic, 4-aminobutyric) or large (all others).

Amino acid substitutions for those indicated in the structure/formula provided can be included In peptide compounds within the scope of the invention and can be classified within this general scheme according to their structure.

In all of the peptides of the invention, one or more amide linkages (—CO—NH—) may optionally be replaced with another linkage which is an isostere such as —$CH_2$NH—, —$CH_2$S—, —$CH_2CH_2$, —CH=CH— (cis and trans), —COCH$_2$—, —CH(OH)CH$_2$— and —CH$_2$SO—. This replacement can be made by methods known in the art. The following references describe preparation of peptide analogs which include these alternative-linking moieties: Spatola, A. F., *Vega Data* (March 1983), Vol. 1, Issue 3, "Peptide Backbone Modifications" (general review); Spatola, A. F., in "Chemistry and Biochemistry of Amino Acids, Peptides and Proteins," B. Weinstein, eds., Marcel Dekker, New York, p. 267 (1983) (general review); Morley, J. S., *Trends Pharm Sci* (1980) pp. 463–468 (general review); Hudson, D., et al., *Int J Pept Prot Res* (1979) 14:177–185 (—$CH_2NH$—, —$CH_2CH_2$—); Spatola, A. F., et al., *Life Sci* (1986) 38:1243–1249 (—$CH_2$—S); Hann, M. M., *J Chem Soc Perkin Trans I* (1982) 307–314 (—CH=CH—, cis and trans); Almquist, R. G., et al., *J Med Chem* (1980) 23:1392–1398 (—$COCH_2$—); Jennings-White, C., et al., *Tetrahedron Lett* (1982) 23:2533 (—$COCH_2$—); Szelke, M., et al., European Application EP 45665; CA:97:39405 (1982) (—CH(OH)$CH_2$—); Holladay, M. W., et al., *Tetrahedron Lett* (1983) 24:4401–4404 (—C(OH)$CH_2$—); and Hruby, V. J., *Life Sci* (1982) 31:189–199 (—$CH_2$—S—).

Preferred Embodiments

In preferred embodiments, the present invention provides compounds of the formula:

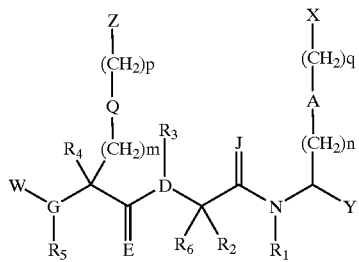

wherein:

m=0,1,2,3,4;

n=0,1,2,3,4;

p=0,1,2,3,4;

q=0,1,2,3,4;

Y=CHO, $COCF_3$, $COCF_2CF_3$, $COCO_2R_7$, $COCONR_8R_9$, $B(OR_{10})_2$; where: $R_7$, $R_8$, $R_9$, $R_{10}$ are the same or different and=H, $C_{1-6}$alkyl, $C_{3-8}$cycloalkyl, aryl$C_{1-3}$alkyl, heteroaryl$C_{1-3}$alkyl;

A=piperdinyl, pyrrolidinyl, cyclopropyl, cyclobutyl, cyclopentyl, cyclohexyl, phenyl, $C_{3-6}$heteroaryl, or is absent;

$R_1$=H or $C_{1-3}$alkyl;

J=O or $H_2$;

$R_2$=H or $C_{1-3}$alkyl;

D=N, CH, $NCH_2$, $NCH_2CH_2$, $CHCH_2$;

$R_3$=H or $C_{1-3}$alkyl;

E=O or $H_2$;

$R_4$=H or $CH_3$;

Q=piperdinyl, pyrrolidinyl, $C_{3-8}$ cycoalkyl, phenyl, substituted phenyl, naphthyl, pyridyl, or is absent;

G=N, CH, or H;

R=H or $C_{1-3}$ alkyl, or is absent if G is H;

$R_6$=H or $CH_3$;

W=H, arylacyl, heteroarylacyl, aryl$C_{1-3}$alkylsulfonyl, arylsulfonyl, substitued arylsulfonyl, aryl$C_{1-4}$alkenylsulfonyl, $C_{1-8}$ alkylsulfonyl, heteroaryl$C_{1-3}$alkylsulfonyl, heteroarylsulfonyl, aryloxycarbonyl, $C_{1-6}$ alkyloxycarbonyl, aryl$C_{1-3}$alkyloxycarbonyl, arylaminocarbonyl, $C_{1-6}$alkylaminocarbonyl, aryl$C_{1-3}$ alkylaminocarbonyl, HOOC—$C_{0-3}$alkylcarbonyl, or is absent if G is H;

X=H, $C_{1-3}$alkyl, NR'R", NH—C(NR'R")=NH, NH—C(NHR')=NR", S—C(NR'R")=NH, S—C(NHR')=NR", C(NR'R")=NH, C(NHR')=NR", or CR'=NR"; where: R',R" are the same or different and =H, $C_{1-6}$alkyl, $C_{1-3}$arylalkyl, aryl or where R'R" forms a cyclic ring containing $(CH_2)_p$ where p=2–5, with the proviso that when X is H or $C_{1-3}$alkyl, then A must contain at least one N atom;

Z=H, $C_{1-3}$alkyl, NR'R", NH—C(NR'R")=NH, NH—C(NHR')=NR", S—C(NR'R")=NH, S—C(NHR')=NR", C(NR'R")=NH, C(NHR')=NR", or CR'=NR"; where: R',R" are the same or different and =H, $C_{1-6}$alkyl, $C_{1-3}$arylalkyl, aryl or where R'R" forms a cydic ring containing $(CH_2)_p$ where p=2–5, with the proviso that when Z is H or $C_{1-3}$alkyl, then Q must contain at least one N atom;

and all pharmaceutically acceptable isomers, salts, hydrates, solvates and prodnug derivatives thereof.

More preferably, compounds of the present invenffon indude those of formula:

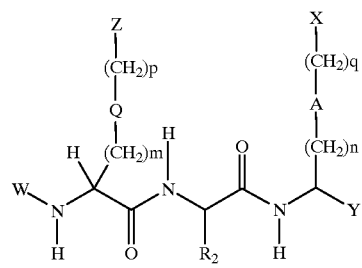

wherein:

m=0,1,2,3,4;

n=0,1,2,3,4;

p=0,1,2,3,4;

q=0,1,2,3,4;

Y=CHO, $COCF_3$, $COCF_2CF_3$, $COCO_2R_7$, $COCONR_8R_9$; where: $R_7,R_8,R_9$ are the same or different and =H, $C_{1-6}$alkyl, $C_{3-8}$cycloalkyl, aryl$C_{1-3}$alkyl, heteroary)$C_{1-3}$alkyl;

A=piperdinyl, pyrrolidinyl, cyclopropyl, cyclobutyl, cyclopentyl, cyclohexyl, phenyl, $C_{3-6}$heteroaryl or is absent, $R_2$=H or $C_{1-3}$alkyl;

Q=piperdinyl, pyrrolidinyl, $C_{3-8}$ cycloalkyl, phenyl, substituted phenyl, naphthyl, pyridyl, or is absent, W=H, arylacyl, heteroarylacyl, aryyl $C_{1-3}$alkylsulfonyl, arylsulfonyl, substituted arylsulfonyl, aryl$C_{1-4}$ alkenylsulfonyl, $C_{1-8}$ alkylsulfonyl, heteroaryl$C_{1-3}$ alkylsulfonyl, heteroarylsulfonyl, aryloxycarbonyl, $C_{1-6}$ alkyloxycarbonyl, aryl$C_{1-3}$alkyloxycarbonyl, arylaminocarbonyl, $C_{1-6}$alkylaminocarbonyl, aryl$C_{1-3}$ alkylaminocarbonyl, or HOOC—$C_{0-3}$aikylcarbonyl;

X=H, $C_{1-3}$alkyl, NR'R", NH—C(NR'R")=NH, NH—C(NHR')=NR", S—C(NR'R")=NH, S—C(NHR')=NR", C(NR'R")=NH, C(NHR')=NR", or CR'=NR"; where: R',R" are the same or different and =H, $C_{1-6}$alkyl, $C_{1-3}$arylalkyl, aryl or where R'R" forms a cyclic ring containing $(CH_2)_p$ where p=2–5, with the proviso that when X is H or $C_{1-3}$alkyl, then A must contain at least one N atom;

Z=H, $C_{1-3}$alkyl, NR'R", NH—C(NR'R")=NH, NH—C(NHR')=NR", S—C(NR'R")=NH, S—C(NHR')=NR", C(NR'R")=NH, C(NHR')=NR", or CR'=NR"; where: R',R" are the same or different and =H, $C_{1-6}$alkyl, $C_{1-3}$arylalkyl, aryl or where R'R" forms a cyclic ring containing $(CH_2)_p$ where p=2-5, with the proviso that when Z is H or $C_{1-3}$alkyl, then Q must contain at least one N atom;

and all pharmaceutically acceptable isomers, salts, hydrates, solvates and prodrug derivatives thereof.

A preferred substituent Y is CHO, $COCO_2R_7$, $COCONR_8R_9$, where: $R_7$, $R_8$, $R_9$, are the same or different and =H, $C_{1-6}$alkyl, $C_{1-8}$cycloalkyl, aryl$C_{1-3}$alkyl, heteroaryl$C_{1-3}$alkyl.

A preferred substituent A is piperdinyl, pyrrolidinyl, cyclopentyl, cydohexyl, phenyl, $C_{3-6}$heteroaryl, or is absent A preferred substituent D is N, CH, $NCH_2$.

A preferred substituent Q is piperdinyl, pyrrolidinyl, $C_{3-8}$ cycloalkyl, phenyl, substituted phenyl.

A preferred substituent W is aryl$C_{1-3}$alkylsulfonyl, arylsulfonyl, substituted arylsulfonyl, aryl$C_{1-4}$alkenylsulfonyl, $C_{1-8}$ alkylsulfonyl, heteroaryl$C_{1-3}$alkylsulfonyl, heteroarylsulfonyl, $C_{1-6}$ alkyloxycarbonyl, aryl$C_{1-3}$alkyloxycarbonyl.

A preferred substituent X is NR'R", NH—C(NR'R")=NH, NH—C(NHR')=NR", S—C(NR'R")=NH, S—C(NHR')=NR", C(NR'R")=NH, C(NHR')=NR"; where: R',R" are the same or different and =H, $C_{1-6}$alkyl.

A preferred substttuent Z is NH—C(NR'R")=NH, NH—C(NHR')=NR", S—C(NR'R")=NH, S—C(NHR')=NR", C(NR'R")=NH, C(NHR')=NR"; where: R',R" are the same or different and =H, $C_{1-6}$alkyl.

Preferred compounds as a whole may be selected from any combination of the formulas presented in this specification with one or more of the preferred groupings of substituents at a particular location.

Some preferred embodiments of the invention are shown in the following Table 1.

TABLE 1

| STRUCTURE | Inhibitory Activity ($IC_{50}$) mM | | |
|---|---|---|---|
| | Factor Xa | Prothrombinase | Thrombin |
| H-D-Arg-Gly-Arg-H | 0.064 | 0.83 | 41 |
| Boc-D-Arg-Gly-Arg-H | 0.050 | 4.0 | >100 |
| HOOCCO-D-Arg-Gly-Arg-H | 0.056 | 0.063 | 95 |
| $HOOCCH_2CO$-D-Arg-Gly-Arg-H | 0.098 | 0.50 | >100 |
| $HOOC(CH_2)_2CO$-D-Arg-Gly-Arg-H | 0.224 | 2.0 | >100 |
| $PhCH_2CH_2CO$-D-Arg-Gly-Arg-H | 0.200 | 1.7 | 75 |
| $PhCH_2SO_2$-D-Arg-Gly-Arg-H | 0.015 | 0.014 | 33 |
| EtOCO-D-Arg-Gly-Arg-H | 0.049 | 0.135 | >100 |
| 2-NaphthoxyAc-D-Arg-Gly-Arg-H | 0.550 | 0.687 | >100 |
| Boc-D-Cit-Gly-Arg-H | 3.0 | 12.0 | >100 |
| Boc-D-Lys-Gly-Arg-H | 10.0 | 68.0 | >100 |
| Boc-D-Har-Gly-Arg-H | 0.100 | 0.173 | 405 |
| Boc-D-Har(($CH_3)_4$)-Gly-Arg-H | 5.0 | 44.0 | >100 |
| Boc-D-Arg-Ala-Arg-H | 0.167 | 0.081 | 5 |
| Boc-D-Arg-D-Ala-Arg-H | 0.230 | 0.800 | >10 |
| Boc-D-Arg-β-Ala-Arg-H | 11.0 | 14.0 | >500 |
| Boc-D-Arg-Aib-Arg-H | 0.552 | 2.0 | >500 |
| Boc-D-Arg-Gly-Arg-CONHEtPh | 0.016 | 0.023 | 4 |

Other preferred embodiments of the invention are shown but are not limited to the following list of compounds, which have the general structure:

W—(Basic amino acid)—(Neutral/small amino acid)—(Arg or Basic amino acid)—Y

Boc-D(2,3-Dap)-Gly-Arg-H
Boc-D-(2,4-Dab)-Gly-Arg-H
γ-Abu-Gly-Arg-H
Boc-D-Orn-Gly-Arg-H
Boc-D-homoLys-Gly-Arg-H
Boc-Bag-Gly-Arg-H
Boc-D-4-Gpa-Gly-Arg-H
Boc-D-3-Gpa-Gly-Arg-H
Boc-D-4Apa-Gly-Arg-H
Boc-D-3-Apa-Gly-Arg-H
Boc-D-4-Acg-Gly-Arg-H
Boc-D(4$NH_2$Phe)-Gly-Arg-H
Boc-D-(3-$NH_2$Phe)-Gly-Arg-H
$BnSO_2$-D-(2,3-Dap)-Gly-Arg-H
$BnSO_2$-D-(2,4-Dab)-Gly-Arg-H
$BnSO_2$-D-Om-Gly-Arg-H
$BnSO_2$-D-homoLys-Gy-Arg-H
$BnSO_2$-Bag-Gly-Arg-H
$BnSO_2$-D-4-Gpa-Gly-Arg-H
$BnSO_2$-D-3-Gpa-Gly-Arg-H
$BnSO_2$-D-4-Apa-Gly-Arg-H
$BnSO_2$-D-3-Apa-Gly-Arg-H
$BnSO_2$-D-4-Acg-Gly-Arg-H
$BnSO_2$-D-(4-$NH_2$Phe)-Gly-Arg-H
$BnSO_2$-D-(3-$NH_2$Phe)-Gly-Arg-H
$BnSO_2$-D-(2,3-Dap)-Gly-Arg-$CONH_2$
$BnSO_2$-D-(2,4-Dab)-Gly-Arg-$CONH_2$
$BnSO_2$-D-Om-GIy-Arg-$CONH_2$
$BnSO_2$-D-homoLys-Gly-Arg-$CONH_2$
$BnSO_2$-Bag-Gly-Arg-$CONH_2$
$BnSO_2$-D-4-Gpa-Gly-Arg-$CONH_2$
$BnSO_2$-D-Gpa-Gly-Arg-$CONH_2$
$BnSO_2$-D-4-Apa-Gly-Arg-$CONH_2$
$BnSO_2$-D-3Apa-Gly-Arg-$CONH_2$
$BnSO_2$-D-4-Acg-Gly-Arg-$CONH_2$
$BnSO_2$-D-(4-$NH_2$Phe)-Gly-Arg-$CONH_2$
$BnSO_2$-D-(3-$NH_2$Phe)-Gly-Arg-$CONH_2$
$BnSO_2$-D-Arg-Gly-(2,4-Dab)-H
$BnSO_2$-D-Arg-Gly-(homoLys)-H
$BnSO_2$-D-Arg-Gly-(4-Gpa)-H
$BnSO_2$-D-Arg-Gly-(3-Gpa)-H
$BnSO_2$-D-Arg-Gly-(4-Apa)-H
$BnSO_2$-D-Arg-Gly-(3Apa)-H
$BnSO_2$-D-Arg-Gly-(4Acg)H
$BnSO_2$-D-Arg-Gly-(4$NH_2$Phe)-H
$BnSO_2$-D-Arg-Gly-(3$NH_2$Phe)-H
Boc-D-3PIA-Gly-Arg-CONHEtPh
Boc-D-4-PIA-Gly-Arg-CONHEtPh
Bac-D-3-GPIA-Gly-Arg-CONHEtPh
Boc-D-4-GPIA-Gly-Arg-CONHEtPh
Boc-D-3-PIG-Gly-Arg-CONHEtPh
Boc-D-4-PIG-Gly-Arg-CONHEtPh
Boc-D-3-GPIG-Gly-Arg-CONHEtPh
Boc-D-4-GPIG-Gly-Arg-CONHEtPh
$BnSO_2$-D-Arg-Gly-Arg-CONHEtPh
$BnSO_2$-D-3-PIA-Gly-Arg-CONHEtPh
$BnSO_2$-D-4-PIA-Gly-Arg-CONHEtPh
$BnSO_2$-D-3-GPIA-Gly-Arg-CONHEtPh
$BnSO_2$-D-4-GPIA-Gly-Arg-CONHEtPh
$BnSO_2$-D-3-PIG-Gly-Arg-CONHEtPh
$BnSO_2$-D-4-PIG-Gly-Arg-CONHEtPh BnSO$_2$-D-3GPIG-Gly-Arg-CONHEtPh
BnSO$_2$-D-4-GPIG-Gly-Arg-CONHEtPh
D-Arg-Gly-Arg-CONHEtPh
D-3-PIA-Gly-Arg-CONHEtPh
D-4-PIA-Gly-Arg-CONHEtPh
D-3-GPlA-Gly-Arg-CONHEtPh
D-4-GPIA-Gly-Arg-CONHEtPh
D-3-PIG-Gly-Arg-CONHEtPh
D-4PIG-Gly-Arg-CONHEtPh
D-3-GPIG-Gly-Arg-CONHEtPh
D-4-GPIG-Gly-Arg-CONHEtPh
BnSO$_2$-D-Arg-Gly-Arg-CON(CH$_2$)$_4$
BnSO$_2$-D-3-PIA-Gly-Arg-CON(CH$_2$)$_4$
BnSO$_2$-D-4PIA-Gly-Arg-CON(CH$_2$)$_4$
BnSO$_2$-D-3-GPIA-Gly-Arg-CON(CH$_2$)$_4$
BnSO$_2$-D-4-GPIA-Gly-Arg-CON(CH$_2$)$_4$
BnSO$_2$-D-3PIG-Gly-Arg-CON(CH$_2$)$_4$
BnSO$_2$-D-4-PIG-Gly-Arg-CON(CH$_2$)$_4$
BnSO$_2$-D-3-GPIG-Gly-Arg-CON(CH$_2$)$_4$
BnSO$_2$-D-4-GPIG-Gly-Arg-CON(CH$_2$)$_4$
Boc-D-Arg-Gly-Arg-CONHBn
Boc-D-3-PIA-Gly-Arg-CONHBn
Boc-D-4-PIA-Gly-Arg-CONHBn
Bac-D-3-GPIA-Gly-Arg-CONHBn
Boc-D-4-GPIA-Gly-ArgCONHBn
Boc-D-3-PIG-Gly-Arg-CONHBn
Boc-D-4-PIG-Gly-Arg-CONHBn
Boc-D-3-GPIG-Gly-Arg-CONHBn
Boc-D-4-GPIG-Gly-Arg-CONHBn
Boc-D-ARG-Gly-Arg-CONHCH$_3$
Boc-D-3-PIA-Gly-Arg-CONHCH$_3$
Boc-D-4-PIA-Gly-Arg-CONHCH$_3$
Boc-D-3-GPIA-Gly-Arg-CONHCH$_3$
Boc-D-4GPIA-Gly-Arg-CONHCH$_3$
Boc-D-3-PIG-Gly-Arg-CONHCH$_3$
Boc-D-4-PIG-Gly-Arg-CONHCH$_3$
Boc-D-3-GPIG-Gly-Arg-CONHCH$_3$
Boc-D-4-GPIG-Gly-Arg-CONHCH$_3$
D-Arg-Gly-Arg-CONHPh
Boc-D-3-PIA-Gly-Arg-CONHPh
Boc-D-4-PIA-Gly-Arg-CONHPh
Boc-D-3-GPIA-Gly-Arg-CONHPh
Boc-D-4-GPlA-Gly-Arg-CONHPh
Boc-D-3-PIG-Gly-Arg-CONHPh
Boc-D-4-PIG-Gly-Arg-CONHPh
Boc-D-3-GPIG-Gly-Arg-CONHPh
Boc-D-4-GPIG-Gly-Arg-CONHPh
BnSO$_2$-D-Arg-Gly-Arg-CONBn
BnSO$_2$-D-3-PIA-Gly-Arg-CONBn
BnSO$_2$-D-4-PIA-Gly-Arg-CONBn
BnSO$_2$-D-GPIA-Gly-Arg-CONBn
BnSO$_2$-D-GPIA-Gly-Arg-CONBn
BnSO$_2$-D-3-PlG-Gly-Arg-CONBn
BnSO$_2$-D-4-PIG-Gly-Arg-CONBn
BnSO$_2$-D-3-GPIG-Gly-Arg-CONBn
BnSO$_2$-D-4-GPIG-Gly-Arg-CONBn The ketoamides synthesized in Examples 42–67, exhibited IC$_{50}$ values in the range of 4–79 nM for Factor Xa and from 5–165 nM for prothrombinase, with selectivities against thrombin of 10–1400.

This invention also encompasses prodrug derivatives of the compounds contained herein. The term "prodrug" refers to a pharmacologically inactive derivative of a parent drug molecule that requires biotransformation, either spontaneous or enzymatic, within the organism to release the active drug. Prodrugs are variations or derivatives of the compounds of this invention which have metabolically cleavable groups and become, by solvolysis under physiological conditions, or by enzymatic degradation the compounds of the invention which are pharmaceutically active in vivo. Prodrug compounds of this invention may be called single, double, triple etc., depending on the number of biotransformation steps required to release the active drug within the organism, and indicating the number of functionalities present in a precursor-type form. Prodrug forms often offer advantages of solubility, tissue compatibility, or delayed release in the mammalian organism (see, Bundgard, H., *Design of Prodrugs*, pp. 7–9, 21–24, Elsevier, Amsterdam 1985 and Silverman, R. B., *The Organic Chemistry of Drug Design and Drug Action*, pp. 352–401, Academic Press, San Diego, Calif., 1992). Prodrugs commonly known in the art indude acid derivatives well known to practitioners of the art, such as, for example, esters prepared by reaction of the parent acids with a suitable alcohol, or amides prepared by reaction of the parent acid compound with an amine, or basic groups reacted to form an acylated base derivative. Moreover, the prodrug derivatives of this invention may be combined with other features herein taught to enhance bioavailability.

In preferred embodiments of the present invention, basic groups such as guanidino or amidino functions are derivatized as carbamates or amides by acylation. Additionally, carbonyl functionalities are derivatized to form various acetals, enol esters, aminals, thioacetals or Shiff's bases using alcohols, thiols, amines or amides, carbamates, substited hydrazines and the like.

Preparation of Compounds

The compounds of the present invention may be synthesized by either solid or liquid phase methods described and referenced in standard textbooks, or by a combination of both methods. These methods are well known in the art. See, Bodanszky, M., In "The Principles of Peptide Synthesis", Hafner, K, Rees, C. W., Trost, B. M., Lehn, J. -M., Schleyer, P. v-R., Zahradnik, R., Eds., Springer-Verlag, Berlin, 1984. Starting materials are commercially available reagents and reactions are carried out in standard laboratory glassware and reaction vessels under reaction conditions of ambient temperature and pressure, except where otherwise indicated.

The peptide aldehyde compounds of the present invention may be synthesized by solution phase procedures described in U.S. Pat. No. 5,380,713 of Balasubramanian et al., or in the European Patent Application EPO 479 489 A2 of Gesellchen et al., or by sequential chemical attachment of amino acid derivatives using the solid phase synthesis reagents and methods disclosed in WO 93/15756 or WO 94/13693.

Peptide alpha-keto acids, esters and amides can be prepared as described by Medhi, G. et al., Biochem. Biophys. Res. Commun., 166 595–600 (1990); Angelastro, et al., J. Med. Chem., 33. 11–13 (1990); or by Webb, T. R. et al., International Patent Application WO 9408941.

Peptide alpha-fluoroketones can be prepared as described by Neises, B., European Patent Application EP 0504064 A1 published Sep. 16, 1992 or described by Skiles, J. W. et, al., J. Med. Chem. 35 641–662 (1992).

Peptide boronic acids and diesters can be prepared by the methods described by Kettner, C. et al., J. Biol. Chem. 265, 18289–18297 (1990).

The starting materials used in any of these methods are commercially available from chemical vendors such as Aldrich, Sigma, Nova Biochemicals, Bachem Biosciences, and the like, or may be readily synthesized by known procedures.

During the synthesis of these compounds, the functional groups of the amino acid derivatives used in these methods are protected by blocking groups to prevent cross reaction during the coupling procedure. Examples of suitable blocking groups and their use are described in "The Peptides: Analysis, Synthesis, Biology", Academic Press, Vol. 3 (Gross, E. & Meienhofer, J., Eds., 1981) and Vol. 9 (1987), the disclosures of which are incorporated herein by reference.

Three exemplary synthesis schemes are outlined directly below, and the specific syntheses are described in the Examples. The reaction products are isolated and purified by conventional methods, typically by solvent extraction into a compatible solvent. The products may be further purified by column chromatography or other appropriate methods.

Scheme 1

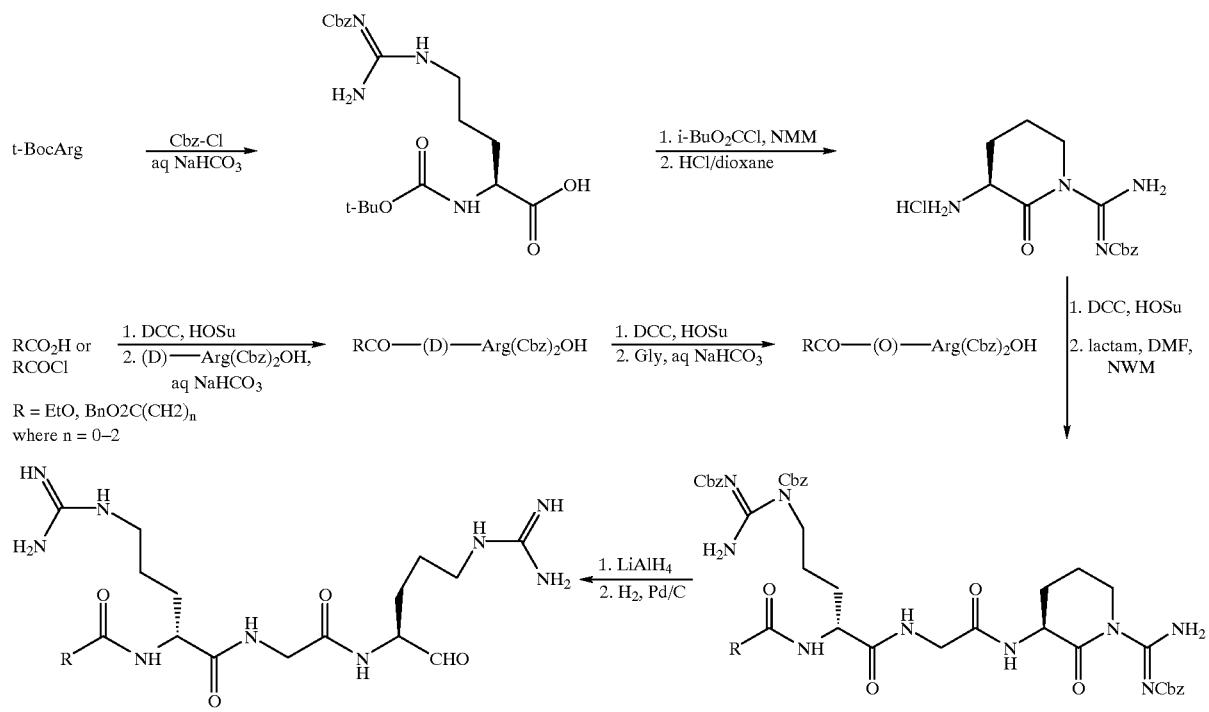

Scheme 2

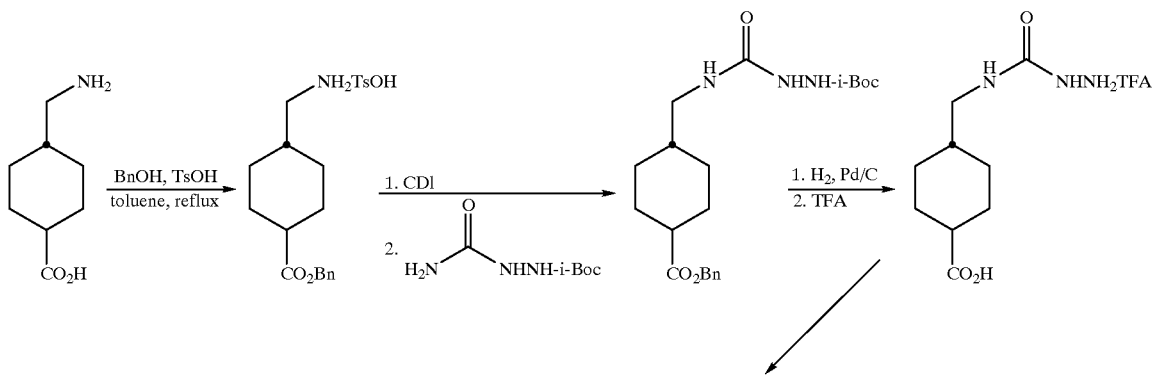

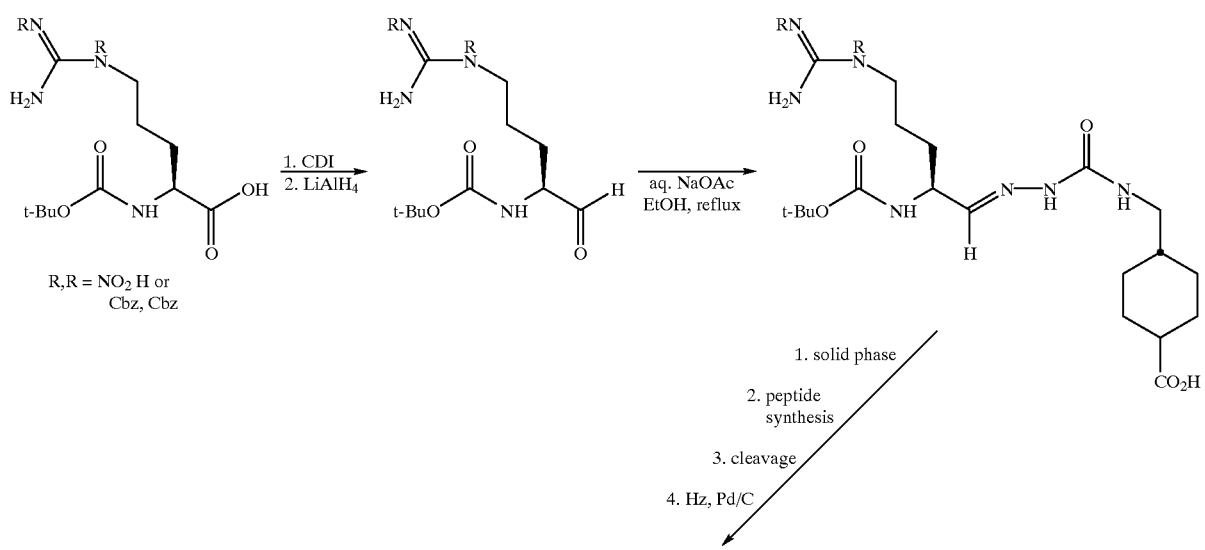
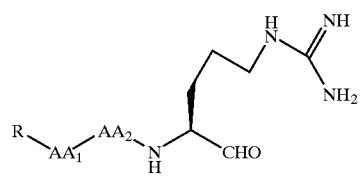
Scheme 3
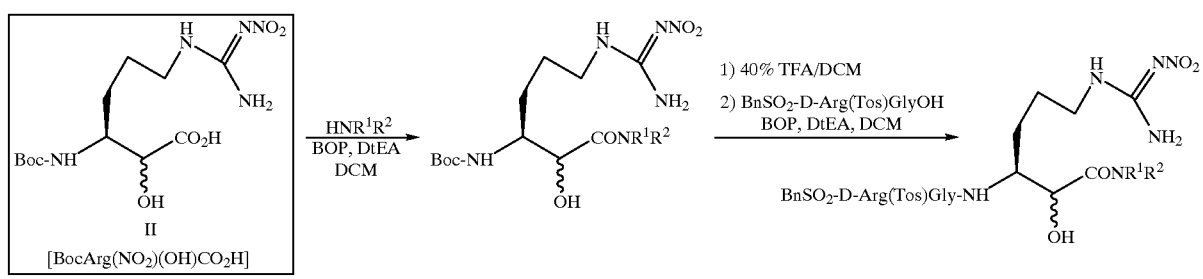

-continued

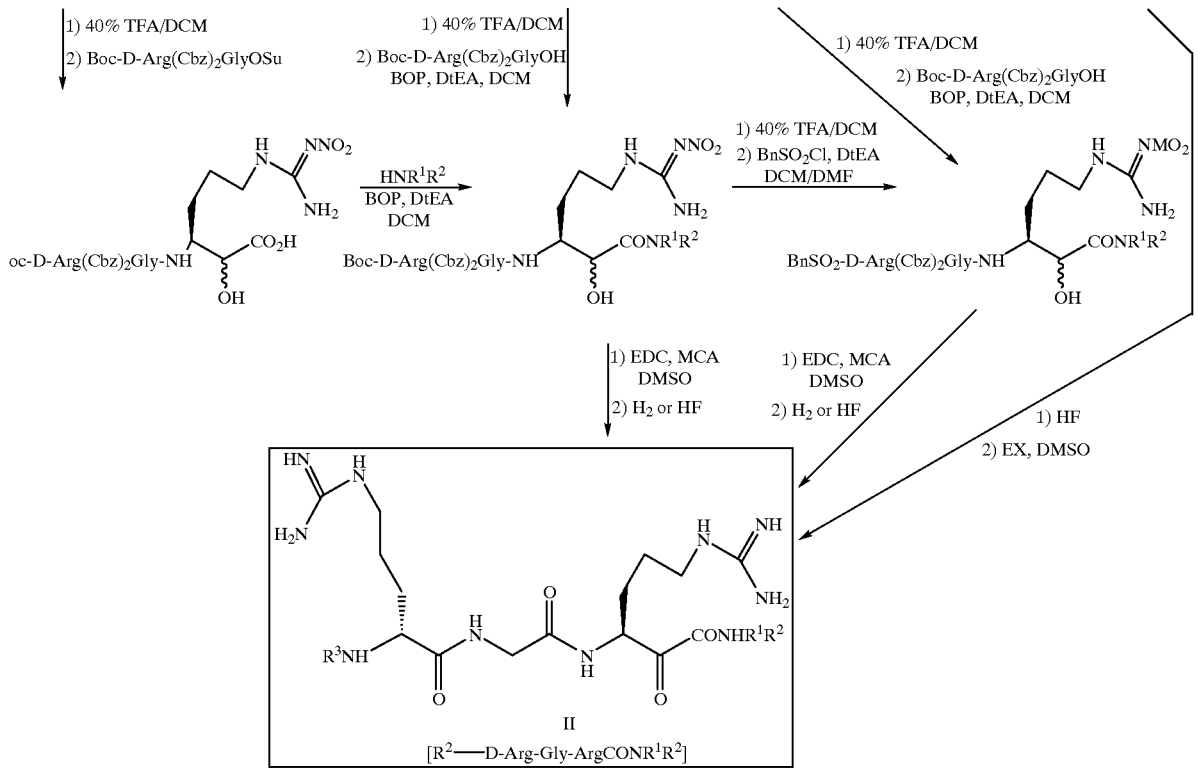

Pharmaceutical and Diagnostic Compositions and Formulations

The compounds of this invention may be isolated as the free acid or base or converted to salts of various inorganic and organic acids and bases. Such salts are within the scope of this invention. Nontoxic and physiologically compatible salts are particularly useful although other less desirable salts may have use in the processes of isolation and purification.

A number of methods are useful for the preparation of the salts described above and are known to those skilled in the art. For example, reaction of the free acid or free base form of a compound of the structures recited above with one or more molar equivalents of the desired add or base in a solvent or solvent mixture in which the salt is insoluble, or in a solvent like water after which the solvent is removed by evaporation, distillation or freeze drying. Alternatively, the free acid or base form of the product may be passed over an ion exchange resin to form the desired salt or one salt form of the product may be converted to another using the same general process.

Diagnostic applications of the compounds of this invention will typically utilize formulations such as solution or suspension. In the management of thrombotic disorders the compounds of this invention may be utilized in compositions such as tablets, capsules or elixirs for oral administration, suppositories, sterile solutions or suspensions or injectable administration, and the like, or incorporated into shaped articles. Subjects in need of treatment (typically mammalian) using the compounds of this invention can be administered dosages that will provide optimal efficacy. The dose and method of administration will vary from subject to subject and be dependent upon such factors as the type of mammal being treated, its sex, weight, diet, concurrent medication, overall clinical condition, the particular compounds employed, the specific use for which these compounds are employed, and other factors which those skilled in the medical arts will recognize.

Formulations of the compounds of this invention are prepared for storage or administration by mixing the compound having a desired degree of purity with physiologically acceptable carriers, excipients, stabilizers etc., and may be prvided in sustained release or timed release formulations. Acceptable carriers or diluents for therapeutic use are well known in the pharmaceutical field, and are described, for example, in *Remington's Pharmaceutcal Sciences,* Mack Publishing Co., (A. R. Gennaro edit. 1985). Such materials are nontoxic to the recipients at the dosages and concentrations employed, and include buffers such as phosphate, citrate, acetate and other organic acid salts, antioxidants such as ascorbic acid, low molecular weight (less than about ten residues) peptides such as polyarginine, proteins, such as serum albumin, gelatin, or immunoglobulins, hydrophilic polymers such as polyvinylpyrrolidinone, amino acids such as glycine, glutamic acid, aspartic acid, or arginine, monosaccharides, disaccharides, and other carbohydrates including cellulose or its derivatives, glucose, mannose or dextrins, chelating agents such as EDTA, sugar alcohols such as mannitol or sorbitol, counterions such as sodium and/or nonionic surfactants such as Tween, Pluronics or polyethyleneglycol.

Dosage formulations of the compounds of this invention to be used for therapeutic administration must be sterile. Sterility is readily accomplished by filtration through sterile membranes such as 0.2 micron membranes, or by other conventional methods. Formulations typically will be stored in lyophilized form or as an aqueous solution The pH of the preparations of this invention typically will be between 3 and 11, more preferably from 5 to 9 and most preferably from 7 to 8. While the preferred route of administration is by injection such as intravenously (bolus and/or infusion), other methods of administration are also anticipated, subcutaneously, intramuscularly, colonically, rectally, nasally or intrapertoneally, employing a variety of dosage forms such as suppositories, implanted pellets or small cylinders, aerosols, oral dosage formulations and topical formulations such as ointments, drops and dermal patches. The compounds of this invention are desirably incorporated into shaped articles such as implants which may employ inert materials such as biodegradable polymers or synthetic silicones, for example, Silastic, silicone rubber or other polymers commercially available.

The compounds of this invention may also be administered in the form of liposome delivery systems, such as small unilamellar vesicles, large unilamellar vesicles and multilamellar vesicles. Liposomes can be formed from a variety of lipids, such as cholesterol, stearylamine or phosphatidylcholines.

The compounds of this invention may also be delivered by the use of antibodies, antibody fragments, growth factors, hormones, or other targeting moieties, to which the compound molecules are coupled. The compounds of this invention may also be coupled with suitable polymers as targetable drug carriers. Such polymers can indude polyvinylpyrrolidone, pyran copolymer, polyhydroxypropyl-methacrylamide-phenol, polyhydroxyethyl-aspartamide-phenol, or polyethyleneoxide-polylysine substituted with palmitoyl residues. Furthermore, the factor Xa inhibitors of this invention may be coupled to a class of biodegradable polymers useful in achieving controlled release of a drug, for example polylactic acid, polyglycolic acid, copolymers of polylaclic and polyglycolic acid, polyepsilon caprolactone, polyhydroxy butyric add, polyorthoesters, polyacetals, polydihydropyrans, polycyanoacrylates and cross linked or amphipathic block copolymers of hydrogels. Polymers and semipermeable polymer matrices may be formed into shaped articles, such as valves, stents, tubing, prostheses and the like.

Therapeutic compound liquid formulations generally are placed into a container having a sterile access port, for example, an intravenous solution bag or vial having a stopper pierceable by hypodermic injection needle.

Therapeutically effective dosages may be determined by either in vitro or in vivo methods. For each particular compound of the present invention, individual determinations may be made to deternine the optimal dosage required. The range of therapeutically effective dosages will naturally be influenced by the route of administration, the therapeutic objectives, and the condition of the patient. For injection by hypodermic needle, it may be assumed the dosage is delivered into the body's fluids. For other routes of administration, the absorption efficiency must be individually determined for each inhibitor by methods well known in pharmacology. Accordingly, it may be necessary for the therapist to titer the dosage and modify the route of administration as required to obtain the optimal therapeutic effect. The determination of effective dosage levels, that is, the dosage levels necessary to achieve the desired result, will be within the ambit of one skilled in the art. Typically, applications of compound are commenced at lower dosage levels, with dosage levels being increased until the desired effect is achieved.

A typical dosage might range from about 0.001 mg/kg to about 1000 mg/kg, preferably from about 0.01 mg/kg to about 100 mg/kg, and more preferably from about 0.10 mg/kg to about 20 mg/kg. Advantageously, the compounds of this invention may be administered several times daily, and other dosage regimens may also be useful.

Typically, about 0.5 to 500 mg of a compound or mixture of compounds of this invention, as the free acid or base form or as a pharmaceutically acceptable salt, is compounded with a physiologically acceptable vehicle, carrier, excipient, binder, preservative, stabilizer, dye, flavor etc., as called for by accepted pharmaceutical practice. The amount of active ingredient in these compositions is such that a suitable dosage in the range indicated is obtained.

Typical adjuvants which may be incorporated into tablets, capsules and the like are a binder such as acacia, corn starch or gelatin, and excipient such as microcrystalline cellulose, a disintegrating agent like corn starch or alginic acid, a lubricant such as magnesium stearate, a sweetening agent such as sucrose or lactose, or a flavoring agent. When a dosage form is a capsule, in addition to the above materials it may also contain a liquid carrier such as water, saline, a fatty oil. Other materials of various types may be used as coatings or as modifiers of the physical form of the dosage unit. Sterile compositions for injection can be formulated according to conventional pharmaceutical practice. For example, dissolution or suspension of the active compound in a vehicle such as an oil or a synthetic fatty vehicle like ethyl oleate, or into a liposome may be desired. Buffers, preservatives, antioxidants and the like can be incorporated according to accepted pharmaceutical practice.

In practicing the methods of this invention, the compounds of this invention may be used alone or in combination, or in combination with other therapeutic or diagnostic agents. In certain preferred embodiments, the compounds of this invention may be coadministered along with other compounds typically prescribed for these conditions according to generally accepted medical practice, such as anticoagulant agents, thrombolytic agents, or other antithrombotics, including platelet aggregation inhibitors, tissue plasminogen activators, urokinase, prourokinase, streptokinase, heparin, aspirin, or warfarin. The compounds of this invention can be utilized in vivo, ordinarily in mammals, such as humans, sheep, horses, cattle, pigs, dogs, cats, rats and mice, or in vitro.

The preferred compounds of the present invention are characterized by their ability to inhibit thrombus formation with acceptable effects on classical measures of coagulation parameters, platelets and platelet function, and acceptable levels of bleeding complications associated with their use. Conditions characterized by undesired thrombosis would include those involving the arterial and venous vasculature.

With respect to the coronary arterial vasculature, abnormal thrombus formation characterizes the rupture of an established atherosclerotic plaque which is the major cause of acute myocardial infarction and unstable angina, as well as also characterizing the occlusive coronary thrombus formation resulting from either thrombolytic therapy or percutaneous transluminal coronary angioplasty (PTCA).

With respect to the venous vasculature, abnormal thrombus formation characterizes the condiion observed in patients undergoing major surgery in the lower extremities or the abdominal area who often suffer from thrombus formation in the venous vasculature resulting in reduced blood flow to the affected extremity and a predisposition to pulmonary embolism. Abnormal thrombus formation further characterizes disseminated intravascular coagulopathy which commonly occurs within both vascular systems during septic shock, certain viral infections and cancer, and is a condition where there is rapid consumption of coagulation factors and systemic coagulation which results in the formation of life-threatening thrombi occurring throughout the microvasculature leading to widespread organ failure.

The compounds of this present invention, selected and used as disclosed herein, are believed to be useful for preventing or treating a condition characterized by undesired thrombosis, such as in (a) the treatment or prevention of any thrombotically mediated acute coronary syndrome including myocardial infarction, unstable angina, refractory angina, occlusive coronary thrombus occurring post-thrombolytic therapy or post-coronary angioplasty, (b) the treatment or prevention of any thrombotically mediated cerebrovascular syndrome including embolic stroke, thrombotic stroke or transient ischemic attacks, (c) the treatment or prevention of any thrombotic syndrome occurring in the venous system including deep venous thrombosis or pulmonary embolus occurring either spontaneously or in the setting of malignancy, surgery or trauma, (d) the treatment or prevention of any coagulopathy including disseminated intravascular coagulation (including the setting of septic shock or other infection, surgery, pregnancy, trauma or malignancy and whether associated with multi-organ failure or not), thrombotic thrombocytopenic purpura, thromboangiitis obliterans, or thrombotic disease associated with heparin induced thrombocytopenia, (e) the treatment or prevention of thrombotic complications associated with extracorporeal circulation (e.g. renal dialysis, cardiopulmonary bypass or other oxygenation procedure, plasmapheresis), (f) the treatment or prevention of thrombotic complications associated with instrumentation (e.g. cardiac or other intravascular catheterization, intra-aortic balloon pump, coronary stent or cardiac valve), and (g) those involved with the fitting of prosthetic devices.

Anticoagulant therapy is also useful to prevent coagulation of stored whole blood and to prevent coagulation in other biological samples for testing or storage. Thus the compounds of this invention can be added to or contacted with any medium containing or suspected to contain factor Xa and in which it is desired that blood coagulation be inhibited, e.g., when contacting the mammal's blood with material such as vascular grafts, stents, orthopedic prostheses, cardiac stents, valves and prostheses, extra corporeal circulation systerns and the like.

Without further description, it is believed that one of ordinary skill in the art can, using the preceding description and the following illustrative examples, make and utilize the compounds of the present invention and practice the claimed methods. The following working examples therefore, specifically point out preferred embodiments of the present invention, and are not to be construed as limiting in any way the remainder of the disclosure.

EXAMPLES

Example 1

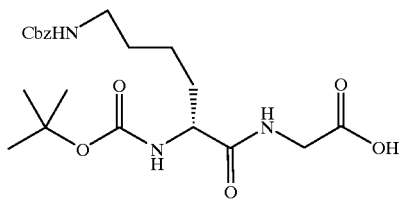

Boc-D-Lys(Cbz)-Gly-OH

To a solution of 1.14 g (3.0 mmol) of Boc-D-Lys(Cbz)-OH and 0.34 g (3.0 mmol) of N-hydroxysuccinimide dissolved in 20 ml of dioxane was added a solution of 0.62 g (3.0 mmol of DCC dissolved in 4.0 ml of dioxane. The resultant solution was stirred at room temperature under a nitrogen atmosphere for 18 hrs, during which time the DCU separated from the solution. After removal of the solids by vacuum filtration, the clear colorless filtrate was treated with a single portion of glycine (0.36 g, 4.9 mmol) and sodium bicarbonate (0.90 g, 10.8 mmol) dissolved in 30 ml of water. The resultant mixture was stirred at room temperature for 2 days. The solution was then acidified to pH=1–2 with 10% HCl solution and exracted with ethyl acetate three times. The combined organic extracts were washed twice with brine, dried over MgSO$_4$, and concentrated in vacuo to afford 1.30 g (3.0 mmol, 100% yield) of the product as a colorless, viscous oil.

RP-HPLC: retention 13.12 min; C$_{18}$, 0-100% CH$_3$CN over 25 minutes, 2.0 ml/min.

NMR (CDCl$_3$): 7.22 (s,C$_6$H$_5$), 4.98 (s,OCH$_2$Ar), 3.95–4.15 (m,NHCH$_2$COOH), 3.80–3.93 (m,NHCHCO), 2.94–3.10 (m,CH$_2$NHCO), 1.00–1.60 (m, CH$_2$CH$_2$CH$_2$),1.30 (s,(CH$_3$)$_3$CO).

Example 2

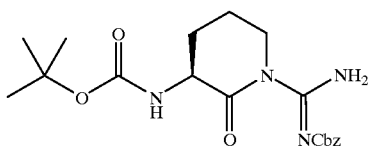

Boc-Arg(Cbz)-lactam

A solution of Boc-Arg(Cbz)-OH (10.6 g, 26.0 mmol) dissolved in 70 ml of dry THF was cooled in a dry ice-acetone bath under a N$_2$ atmosphere N-Methylmorpholine (6.5 ml, 59.1 mmol) was added to the solution followed by isobutyl chloroformate (3.8 ml, 29.3 mmol). A white solid separated immediately, and the suspension was stirred at the temperature of the dry ice-acetone bath for 1 hr, warmed to room temperature and stirred an additional 2.5 hrs. The mixture was poured onto ice-water and the precipitated solid collected and dried in vacuo. There was obtained 8.35 g (21.4 mmol, 82% yield) of the product as a white solid.

RP-HPLC: retention 15.09 min; C$_{18}$, 0-100% CH$_3$CN over 25 minutes, 2.0 ml/min.

NMR (CDCl$_3$): 9.4–9.7 (bm,NH),7.30–7.50 (m, C$_6$H$_5$),5.25–5.35 (d,NHCH),5.20 (s,OCH$_2$Ar), 4.80–5.00 (m,NCHCH$_2$), 3.30–3.60/4.30–4.60 (m,N CH$_2$),1.80–2.10/240–2.60 (m,CH$_2$CH$_2$). 1.50 (s,(CH$_3$)$_3$CO).

IR: 3346 cm$^{-1}$, 3273 cm$^{-1}$, 3244 cm$^{-1}$, 1,726 cm$^{-1}$, 1698 cm$^{-1}$, 1644 cm$^{-1}$.

Example 3

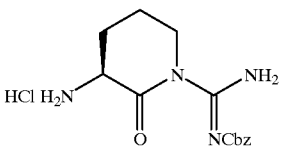

Arc(Cbz)-lactam-HCl salt

Boc-Arg(Cbz)-lactam (1.20 g, 3.1 mmol prepared in Example 2 was treated with 10 ml of 4N HCl/dioxane for 1 hr at room temperature under N$_2$. Removal of solvent in vacuo produced a white glass. This material was triturated with ether and filtered to afford 1.05 g (3.2 mmol, 100% yield) of a non-hygroscopic white powder.

Example 4

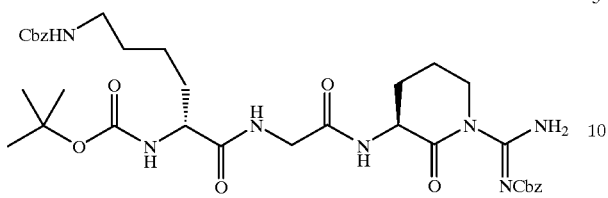

Boc-D-Lys(Cbz)-Gly-Arg(Cbz)-lactam

To a solution of 1.30 g (3.0 mmol) of Boc-D-Lys(Cbz)-Gly-OH prepared in Example 1, in 30 ml of dioxane was added N-hydroxysuccinimide (0.35 g,3.0 mmol), followed by a solution of DCC (0.63 g, 3.0 mmol) in 5 ml of dioxane. The resultant solution was stirred at room temperature under $N_2$ for 17 hrs, during which time DCU precpitated. After removal of solids by vacuum filtration, the clear, colorless filtrate was concentrated to dryness in vacuo to yield a colorless oil. This material was dissolved in 25 ml of DMF and treated with the Arg(Cbz)-lactam-HCl salt of Example 3 (0.98 g, 3.0 mmol) which was added as a solid followed by the addition of 25 ml of DMF. After the lactam had dissolved completely, N-methylmorpholine (1.0 ml, 9.1 mmol) was added to neutralize the lactam salt. The clear colorless solution was stirred at room temperature under $N_2$ for 25 hrs. The resultant yellow solution was acidified to pH=1–2 with 10% HCl solution and extracted twice with ethyl acetate. The combined organic extracts were washed six times with brine, dried over $MgSO_4$ and concentrated in vacuo. There was obtained 1.39 g (2.0 mmol, 65% yield) of a white solid product.

RP-HPLC: retention 14.46 min; $C_{18}$, 0-100% $CH_3CN$ over 25 minutes, 2.5 ml/min.

MS: 710 by thermospray; calculated (M+H)=710.8.

Example 5

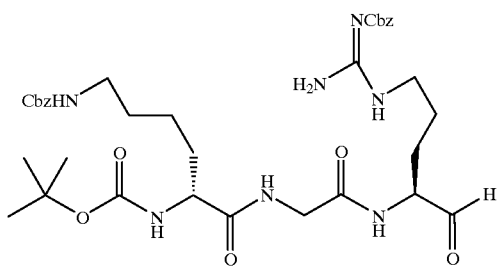

Boc-D-Lys(Cbz)-Gly-Arg(Cbz)-H

To a dry flask equipped with a $N_2$ inlet, low temperature thermometer, and rubber septum was introduced a solution of Boc-D-Lys(Cbz)-Gly-Arg(Cbz)-lactam (1.37 g, 1.9 mmol) prepared in Example 4, dissolved in 50 ml of anhydrous THF. The flask was cooled in a $CCl_4$-dry ice bath such that the internal temperature was maintained between $-35\_C.$ and $-25\_C.$ To the cooled solution was added $LiAlH_4/THF$ (1.0 M solution) (1.9 ml, 1.9 mmol). The resultant solution was stirred in the cold under $N_2$ for 2 hr. After this time, the reaction was quenched by introduction of 5 ml of $CH_3OH$ to the chilled solution, followed by gradual warming to ambient temperature. Sulfuric acid solution (1 N, 36 ml) was added and extracted with ethyl acetate. The organic phase was washed twice with brine, dried over $MgSO_4$, and concentrated in vacua. There was obtained 1.23 g (1.7 mmol, 89% yield) of the product as a white solid.

RP-HPLC: retention 13.34 min; retention time 13.41 min (thiosemicarbazone); $C_{18}$, 0-100% $CH_3CN$ over 25 minutes, 2.0 ml/min.

MS: M+H=712 by thermospray; calculated (M+H)=712.8.

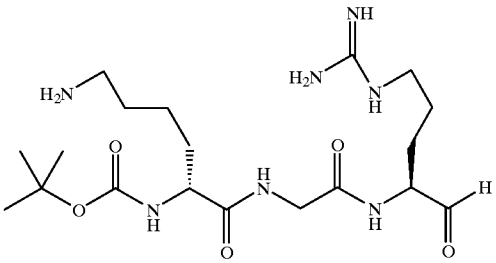

Boc-D-Lys-Gly-Arg-H

A Parr bottle was charged with Boc-D-Lys(Cbz)-Gly-Arg(Cbz)-H prepared In Example 5, (1.21 g, 1.7 mmol), 10% palladium on carbon (0.43 g, 0.4 mmol) and 35 ml of absolute ethanol. Hydrogenation was conducted at 40 psi in a Parr shaker for 24 hrs after which the catalyst was removed by vacuum filtration over Celite. The clear colorless fitrate was diluted with water and acetic acid (1 ml) and lyophilized. The lyophilized powder was purified by preparative RP-HPLC using a gradient from 10% $CH_3CN$ in water (containing 0.1% TFA) to 50% $CH_3CN$ in water (containing 0.1% TFA) using a flow rate of 10 ml/min. The desired fractions were combined and lyophilized to yield 0.16 g (0.35 mmol, 20% yield) of the product as a white powder.

RP-HPLC: retention 8.66 min and 9.26 min (tautomers); retention time 8,7 min (thiosemicarbazone); $C_{18}$, 0-100% $CH_3CN$ over 25 minutes, 2.0 ml/min.

MS: M+H=444 by thermospray; calculated (M+H)=444.5.

Example 7

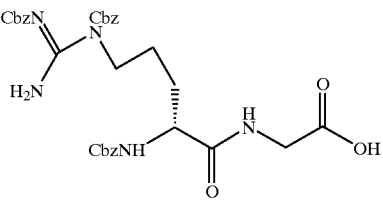

Cbz-D-Arg(Cbz)$_2$-Gly-OH

Cbz-D-Arg(Cbz)$_2$-Gly-OH is prepared according to Example 1 by coupling the N-hydroxysuccinimide active ester of Cbz-D-Arg(Cbz)$_2$-OH to glycine in a yield of 87%.

RP-HPLC: retention 14.09 min; $C_{18}$, 0-100% $CH_3CN$ over 25 minutes, 2.0 ml/min.

MS: (M+H)=634.4 by electrospray; calculated (M+H)=634.7.

Example 8

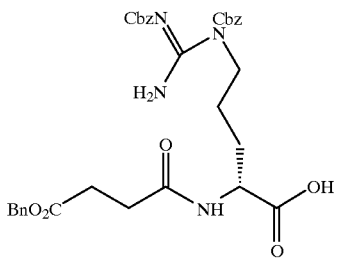

BnOSuc-D-Arg(Cbz$_2$)-OH

To a solution of 186 mg (0.89 mmol) of succinic acid monobenzyl ester and 113 mg (1.0 mmol) of N-hydroxysuccinimide in 1.7 mL of p-dioxane is added 194 mg (0.93 mmol) of DCC in 0.5 mL of dioxane. The solution is allowed to stir for 18 hr. The white precipitate of DCU is filtered and the solution is added dropwise to 4.5 mL of 0.6M NaHCO$_3$ containing 485 mg (0.89 mmol) of H-D-Arg(Cbz$_2$)-OH (prepared by treatment of Boc-D-Arg(Cbz$_2$)-OH with TFA for 1 h followed by concentration in vacuo). After stirring for 24 h at 23° C., the reaction was diluted with 1N HCl and extracted 3 times with EtOAc. The organic layers were combined and washed with brine, dried (MgSO4), and concentrated (in vacuo) to give 516 mg (91%) of a clear oil.

NMR-90 MHz (CDCl$_3$): 7.6–7.2 (br s,15), 5.3 (s,2), 5.2 (s,2), 5.1 (s,2), 4.5 (m,1), 3.5 (br m, 2), 2.4 (br m, 4), 1.8 (br m, 4).

RP-HPLC: retention 14.94 min; C$_{18}$, 0-100% CH$_3$CN over 25 minutes, 2.0 ml/min.

MS: (M+H)=633.6 by electrospray; calculated (M+H)=633.7.

Example 9

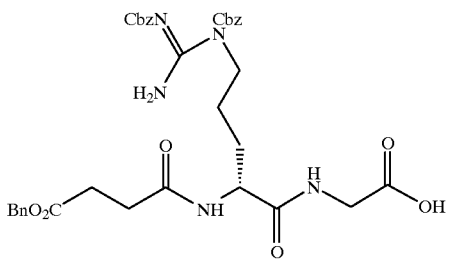

BnOSuc-(D-Arg)$_2$-Gly-OH

O-benzylsuccinoyl-D-arginyl(Cbz$_2$)-glycine is prepared according to Example 1 by coupling the N-hydroxysuccinimide active ester of O-benzylsuccinoyl-D-arginine(Cbz$_2$)-OH to glycine in a crude yield of 81%. This material was purified by flash silica gel chromatography eluting with 0, 2.5, 5, 7.5, and 10% methanol/DCM.

RP-HPLC: retention 13.92 min; C$_{18}$, 0-100% CH$_3$CN over 25 minutes, 2.0 ml/min.

MS: (M+H)=690.8 by electrospray; calculated (M+H)=690.7.

Example 10

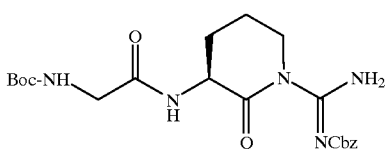

Boc-Gly-Arg(N-Cbz)-lactam

To a solution of Boc-Gly (173 mg, 1.1 mmol) and the Arg(Cbz)4lactam-HCl salt of Example 3 (330 mg, 1.0 mmol) in 2 mL of 1:1 hexane/THF at 0° C. is added BOP (472 mg, 1.0 mmol) followed by 191 μL of DIEA (1.1 mmol). The solution is allowed to warm to 23° C. and stir for 3 hrs at which time the solvent is removed in vacuo. The residue is dissolved in 10 mL of EtOAc and extracted twice with sat. NaHCO$_3$, twice with 5% H$_3$PO$_4$, dried (Na$_2$SO$_4$), and concentrated (in vacuo) to afford a 80–95% yield of the product as a white solid.

RP-HPLC retention, 13.92 min, linear gradient 30% water/TEAP(pH 2.5) to 100% CH$_3$CN over 30 min at 1.5 ml/min.

MS: (M+H)=873.0 by electrospray; calculated (M+H)=873.0.

Example 11

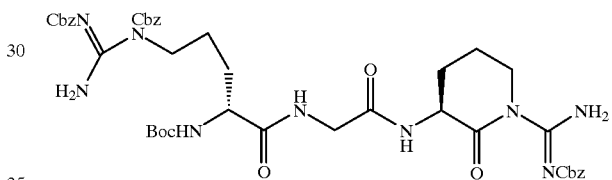

Boc-D-Arg-(Cbz$_2$)-Gly-Arg(N-Cbz)-lactam

Boc-D-Arg(Cbz$_2$)-Gly-Arg(N-Cbz)-lactam is prepared by coupling H-Gly-Arg(Cbz$_2$)-lactam (prepared by deprotection of Boc-Gly-Arg(Cbz$_2$)-lactam with 40% TFA/DCM at 23° C. over 1 h and concentration in vacuo) to the tert-butyloxycarbonyl-D-Arg(Cbz$_2$)-OH according to the procedure in example 10. The product was obtained in 90% yield as a white solid.

RP-HPLC retention, 13.92 min, linear gradient 30% H$_2$O/TEAP(1% TEA/1% H$_3$PO$_4$, pH 2.5) to 100% CH$_3$CN over 30 min at 1.5 mL/min.

MS: (M+H)=873.0 by electrospray; calculated (M+H)=873.0.

Example 12

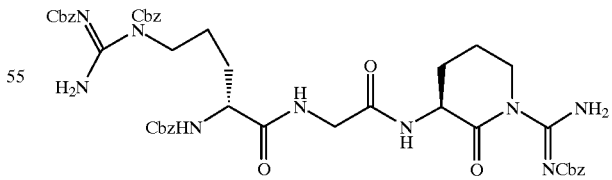

Cbz-D-Arg(Cbz$_2$)-Gly-Arg(Cbz)-lactam

Benzyloxycarbony-D-Arg(Cbz$_2$)-Gly-Arg(Cbz)-lactam is prepared by coupling H-Arg(Cbz$_2$)-lactam to the N-hydroxysuccinimide active ester of benzyloxycarbonyl-D-Arg(Cbz$_2$)-Gly-OH according to the procedure in Example 4. The crude oil obtained after extraction was purified by flash silica gel chromatography eluting with 0, 2.5, 5, 6% MeOH/DCM. The appropriate fractions were combined and concentrated in vacuo to yield 37% of a white solid:

RP-HPLC retention, 14.60 min; $C_{18}$, 0-100% $CH_3CN$ over 25 minutes, 2.0 ml/min.

MS: (M+H)=906.6 by electrospray; calculated (M+H)= 906.9.

Example 13

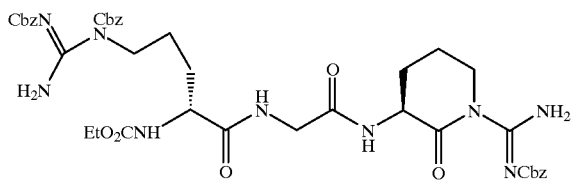

$EtO_2C$-D-Arg($Cbz_2$)-Gly-Arg(Cbz)-lactam

Ethoxycarbonyl-D-Arg($Cbz_2$)-Gly-Arg-(Cbz)-lactam is prepared by coupling H-Arg($Cbz_2$)-lactam to the N-hydroxysuccinimde active ester of ethoxycarbony-D-Arg-Gly-OH according to the procedure in Example 4. The crude oil obtained after extraction was purified by flash silica gel chromatography eluting with 0, 2.5, 5, 10% MeOH/DCM. The appropriate fractions were combined and concentrated in vacuo to yield 46% of a white solid:

RP-HPLC retention, 14.13 min; $C_{18}$, 0-100% $CH_3CN$ over 25 minutes, 2.0 ml/min.

MS: (M+H)=844.1 and (M+H+thioglycerol)=952.1 by fast atom bombardment; calculated (M+H)=844.4.

Example 14

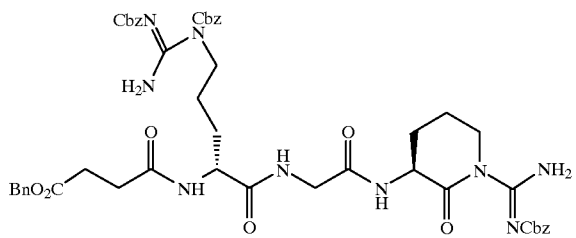

O-Benzylsuccinoyl-D-Arg($Cbz_2$)-Gly-Arg(Cbz)-lactam

O-Benzylsuccinoyl-D-Arg($Cbz_2$)-Gly-Arg(Cbz)-lactam is prepared by coupling of H-Arg($Cbz_2$)lactam to the succinimide active ester of O-benzylsuccinyl-D-Arg($Cbz_2$)-Gly-OH according to the procedure in Example 4. The crude oil obtained after extraction was purified by flash silica gel chromatography eluting with 0, 2.5, 5, 10% MeOH/DCM. The appropriate fractions were combined and concentrated in vacuo to yield 41% of a white solid:

RP-HPLC retention, 14.54 min; $C_{18}$, 0-100% $CH_3CN$ over 25 minutes, 2.0 ml/min.

MS: (M+H)=963.1 by electrospray; calculated (M+H)= 963.06.

Example 15

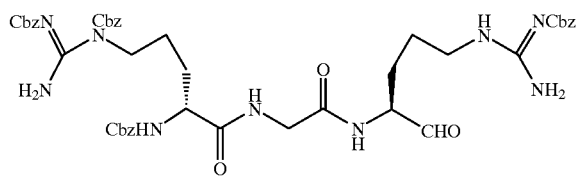

Cbz-D-Arg($Cbz_2$)-Gly-Arg(Cbz)-H

Cbz-D-Arg($Cbz_2$)-Gly-Arg(Cbz)-H is prepared by reduction of the corresponding lactbm in 77% yield according to the procedure in Example 5.

RP-HPLC: retention 13.9 and 14.1 min (tautomers); 14.2 min (thiosemicarbazone derivative); $C_{18}$, 0-100% $CH_3CN$ over 25 minutes, 2.0 mL/min.

MS:(M+H)=908.6 and (M+$NH_4$)=926.8, calculated (M+H)=908.9.

Example 16

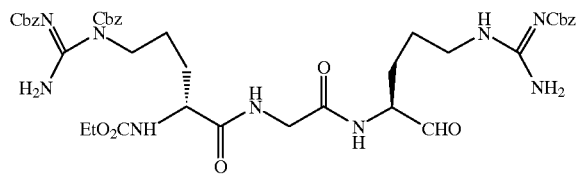

$EtO_2C$-D-Arg($Cbz_2$)-Gly-Arg(Cbz)-H $EtO_2C$-D-Arg($Cbz_2$)-Gly-Arg(Cbz)-H is prepared by reduction of the corresponding lactam as prepared in Example 13 in 68% yield according to the procedure in Example 5.

RP-HPLC retention, 13.9 and 14.1 min (tautomers);14.2 min (thiosemicarbazone derivative); $C_{18}$, 0-100% $CH_3CN$ over 25 minutes, 2.0 mL/min.

MS: (M+H)=846.5 and (M+$NH_4$)=864.5 by fast atom bombardment, calculated (M+H)=846.9.

Example 17

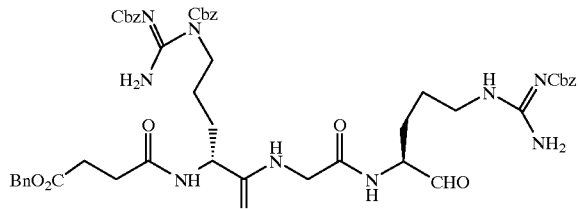

O-Benzylsuccinoyl-D-Arg($Cbz_2$)l-Gly-Arg(Cbz)-H

O-Benzylsuccinoyl-D-Arg($Cbz_2$)-Gly-Arg(Cbz)-H is prepared by reduction of the corresponding lactam, as prepared in Example 14 in 89% yield according to the procedure in Example 5.

RP-HPLC retention, 13.74 and 13.97 min (tautomers), 13.87 min (thiosemicarbazone derivative); $C_{18}$, 0-100% $CH_3CN$ over 25 minutes, 2.0 mL/min.

MS:(M+H)=965.2 by electrospray, calculated (M+H)= 965.1.

Example 18

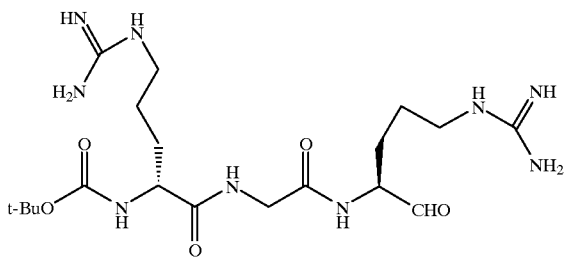

Boc-D-Arg-Gly-Arg-H

Boc-D-Arg-Gly-Arg-H was prepared by hydrogenolysis of the corresponding protected peptide aldehyde Cbz-D-Arg(Cbz$_2$)-Gly-Arg(Cbz)-H (prepared by reduction of the corresponding lactam of Example 11 in 77% yield according to the procedure in Example 5 and deprotected directly without further purification or characterization) following the procedure in Example 6 except that THF/hexane was used as solvent. After 1 h, the deprotection is complete and the catalyst is removed by vacuum filtration through Celite. The compound is then purified by preparative reversed-phase HPLC using a gradient of 100% water/0.1% TFA to 50% CH$_3$CN/0.1% TFA. The appropriate fractions are pooled and lyophilized to give the desired product as white solid.

RP-HPLC retention: 8.58 and 8.65 min (tautomers); 6.68 min (semicarbazone derivative); C$_{18}$, 0-100% CH$_3$CN over 25 minutes, 2.0 mL/min.

MS: (M+H)=472.3 by fast atom bombardment, calculated (M+H)=472.3.

Example 19

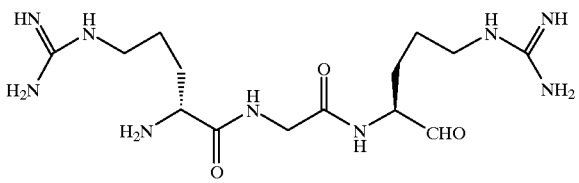

D-Arg-Gly-Arg-H

D-Arg-Gly-Arg-H was prepared by hydrogenolysis of the corresponding protected peptide aldehyde Cbz-D-Arg(Cbz$_2$)-Gly-Arg(Cbz)-H as prepare in Example 15 following the procedure in Example 6. After 1 h, the deprotection is complete and the catalyst is removed by vacuum filtration through Celite. The pH of the solution is adjusted to 5 using Biorad WGR-2 (free amine form), filtered and lyophilized to give the desired product as white solid in 84% yield.

RP-HPLC retention: 2.55 min; 2.87 min (thiosemicarbazone derivative); C$_{18}$, 0-100% CH$_3$CN over 25 minutes, 2.0 mL/min.

MS: (M+H)=372.1 by electrospray, calculated (M+H)=372.5.

Example 20

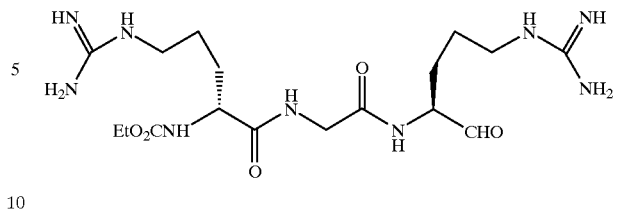

EtO$_2$C-D-Arg-Gly-Arg-H

EtO$_2$C-D-Arg-Gly-Arg-H was prepared by hydrogenolysis of the corresponding protected peptide aldehyde of Example 16 following the procedure in Example 6 except that 0.1M THF and 0.2M aqueous acetic acid was used as solvent. After 1 h, the deprotection is complete and the catalyst is removed by vacuum filtration through Celite. The solution is lyophilized to give the desired product as white solid in 71% yield.

RP-HPLC retention, 8.5 and 8.7 min (tautomers); 8.9 min (thiosemicarbazone derivative); C$_{18}$, 0-100% CH$_3$CN over 25 minutes, 2.0 mL/min.

MS: (M+H)=444.2 by fast atom bombardment, calculated (M+H)=444.3.

Example 21

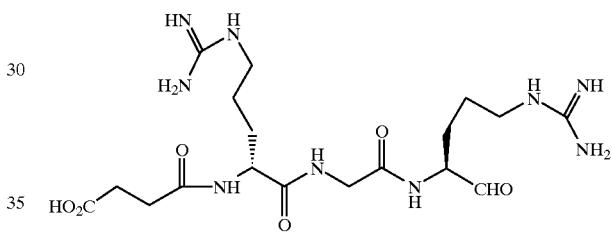

Succinoyl-D-Arg-Gly-Arg-H

Succinoyl-D-Arg-Gly-Arg-H was prepared by hydrogenolysis of the corresponding protected peptide aldehyde of Example 17 following the procedure in Example 6. After 1 h, the deprotection is complete and the catalyst is removed by filtration through Celite. The solution is lyophilized to give the desired product as white solid in 49% yield.

RP-HPLC retention: 3.02 min; 3.51 min (thiosemicarbazone derivative); 12.55 min (2,4 dinitrophenyl-hydrazone derivative); C$_{18}$, 0-100% CH$_3$CN over 25 minutes, 2.0 mL/min.

MS: (M+H)=472.8 by electrospray, calculated (M+H)=472.5.

Example 22

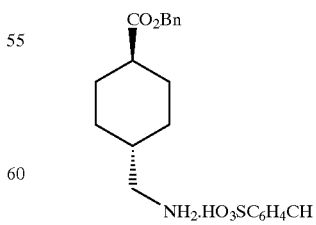

Benzyl trans4-aminomethylcyclohexane1-carboxylate-p-toluenesulfonic acid salt

A mixture of 10.0 g (63.6 mmol) of trans-4-aminomethylcyclohexane-1-carboxylic acid, 25.1 g (132 mmol) of 4-toluenesulfonic acid, 50 mL (482 mmol) of benzyl alcohol, and 75 mL of toluene was heated to reflux under a $N_2$ atmosphere using a Dean-Stark trap to collect water formed during the reaction. During reflux, all solids dissolved to leave a colorless solution. After 3 hours at reflux, the solution began to turn yellow. Heat was removed, and the flask allowed to cool to room temperature. The solids which separated out were collected and washed with diethyl ether. There was obtained 24.5 g (58.4 mmol, 92% yield) of product as a white solid.

NMR (CD$_3$OD): 7.12/7.20/7.65/7.73 (ABq, C$_6$<u>H</u>$_4$); 7.26 (s, C$_6$<u>H</u>$_5$); 5.06 (s, OC<u>H</u>$_2$C$_6$H$_5$); 2.72/2.80 (d, C<u>H</u>$_2$N); 2.32 (s, ArC<u>H</u>$_3$); 100–2.18 (m, cyclohexyl <u>H</u>)

MS: M$^+$=247 by electron-impact; calculated M$^+$=247.3.

Example 23

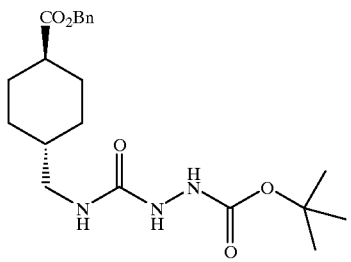

Benzyl trans-4-(tertbutoxycarbonylhydrazidocarbonyl)-aminomethylcyclohexane-1-carboxylate:

To a solution of 3.24 g (20.0 mmol) of carbonyl diimidazole dissolved in 50 mL of DMF was added over 40 minutes a solution of 2.65 g (20.0 mmol) of tert-butylcarbazate dissolved in 50 mL of DMF. The resultant solution was stirred at room temperature under a $N_2$ atmosphere for 10 minutes. A solution of 7.16 g (17.1 mmol) of benzyl trans-4-aminomethylcyclohexane-1-carboxylate.TsOH dissolved in 50 mL of DMF was then added over 65 minutes. Finally, after the above solution was stirred for 5 min, 10 mL (71.7 mmol) of triethylamine was added over a 5 minute period. The resultant light yellow solution was stirred for 18½ hrs.

The solution was acidified with the addiion of 10% HCl, transferred to a separatory funnel, and extracted twice with ethyl acetate. The combined organic extracts were washed three times with saturated brine, dried over MgSO$_4$, and concentrated in vacuo. Under high vacuum, there was obtained 6.64 g (16.4 mmol, 96% yield) of product as a sticky, yellow foam.

RP-HPLC: retention time=13.73 min; C$_{18}$, 0–100% CH$_3$CN over 25 minutes, 2.0 mL/min.

NMR (CDCl$_3$): 7.25 (s, C$_6$<u>H</u>$_5$); 6.67/6.72 (2 s, N<u>H</u>×2); 5.50–5.62 (t, N<u>H</u>CH$_2$); 5.00 (s, OC<u>H</u>$_2$C$_6$H$_5$); 2.95–3.05 (t, C<u>H</u>$_2$N); 0.80–2.20 (m, cyclohexyl <u>H</u>); 1.36 (s, (C<u>H</u>$_3$)$_3$CO)

Example 24

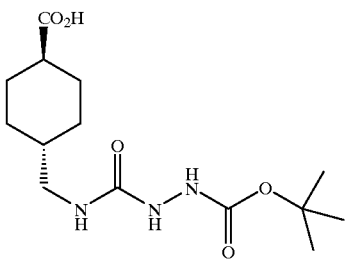

trans-4-(tertbutoxycarbonylhydrazidocarbonyl) aminomethylcyclohexane-1-carboxylic acid A Parr Bottle was charged with 5.46 g (13.2 mmol) of benzyl trans-4-(tertbutoxycarbonylhydrazidocarbonyl)-aminomethylcyclohexane-1-carboxylate dissolved in 60 mL of methanol. Added was 0.50 g (0.47 mmol) of 10% palladium on carbon catalyst. After hydrogenation at 38 psi on a Parr shaker for 90 minutes, the catalyst was removed by vacuum filtration over Celite. Concentration in vacuo of the filtrate gave 4.22 g (13.3 mmol, 100%) of product as a white solid.

IR: 3308 cm$^{-1}$, 3276 cm$^{-1}$, 1732 cm$^{-1}$, 1720 cm$^{-1}$, 1704 cm$^{-1}$

MS: M+H=316 by DCl; calculated (M+H)=316.3.

Example 25

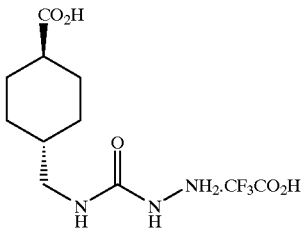

trans-4-(hydrazidocarbonyl)aminomethylcylohexane-1-carboxylic acid, trifluoroacetate salt:

A solution of 3.92 g (12.4 mmol of trans-4-(tertbutoxycarbonylhydrazidocarbonyl)-aminomethylcydohexane-1-carboxylic acid dissolved in 25 mL of TFA and 25 mL of DCM was stirred at room temperature under a $N_2$ atmosphere for 90 minutes. Solvent was removed in vacuao to leave a viscous, pale yellow oil. Addition of ethanol induced solidification. The solid was collected and washed with diethyl ether to produce 2.19 g (6.65 mmol, 54% yield) of product as a white solid.

RP-HPLC: retention time=2.87 minutes; C$_{18}$, 0–100% CH$_3$CN over 25 minutes, 2.0 mL/min.

IR: 3357 cm-hu −1, 3264 cm$^{-1}$, 1705 cm$^{-1}$, 1886 cm$^{-1}$

Example 26

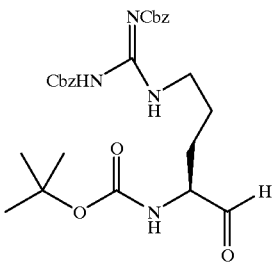

Boc-Arg(Cbz)₂H:

A solution of 2.72 g (5.00 mmol) of Boc-Arg(Cbz)₂-OH and 0.81 g (5.00 mmol) of CDI dissolved in 40 mL of anhydrous THF was stirred at room temperature under a $N_2$ atmosphere for 3 hrs. The flask was cooled in a dry ice/acetone bath and 5.0 mL (5.00 mmol) of 1 Molar LiAlH₄ (in THF) was added by syringe. The solution was stirred in the cold bath for 3 hours, then quenched by addition of 10 mL of 10% HCl solution. The flask was then removed from the cold bath.

After the flask warmed to room temperature, the contents were transferred to a separatory funnel, diluted with additional 10% HCl and extracted twice with ethyl acetate. The combined organic extracts were washed three times with saturated brine, dried over MgSO₄, and concentrated in vacuo. Under high vacuum, there was obtained 2.69 g (5.10 mmol, 102% yield) of product as a white foam.

RP-HPLC: retention time =13.28 min; 13.43 min (thiosemicarbazone); $C_{18}$, 0-100% $CH_3CN$ over 25 minutes, 2.0 mL/min.

MS: M+H=527 by DCI; calculated (M+H)=527.5.

Example 27

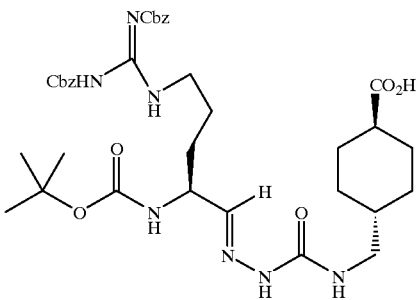

$N_\alpha$-Boc(Cbz₂)Argininal semicarbazonyl-$N_2$-trans-4-methylenecyclohexane-1-carboxylic acid:

A solution of 2.69 g (5.10 mmol) of Boc-Arg(Cbz)₂-H, 2.17 g (6.60 mmol) of trans-4-(hydrazidocarbonyl) aminomethylcyclohexane-1-carboxylic acid trifluoroacetate salt, 1.30 g (9.53 mmol of sodium acetate, 75 mL of ethanol, and 75 mL of water was refluxed for 2¼ hrs. The solution was allowed to cool to room temperature, during which time the flask contents became cloudy.

After acidification to pH=1 with 50 mL of 10% HCl, the solution was extracted three times with ethyl acetate. The combined organic extracts were washed once with saturated brine solution, dried over MgSO₄, and concentrated in vacuo. Under high vacuum, there was obtained 2.78 g (3.84 mmol, 75% yield) of product as a pale yellow, microcrystalline foam.

RP-HPLC: retention time=14.11 minutes; $C_{18}$, 0-100% $CH_3CN$ over 25 minutes, 2.0 mL/min.

NP-HPLC: retention time=21.50 minutes (gradient from 100% Dichloromethane to 4:1 Dichloromethane: Methanol over 40 minutes)

MS: M+H=724 by electrospray; calculated (M+H)= 724.8.

Example 28

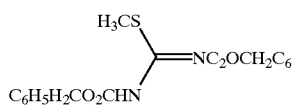

$N_1$, $N_2$-(Cbz)₂-S-methylisothiourea:

To a suspension of 10.02 g (36.0 mmol) of S-methylisothiourea in 100 mL of DCM was added 10 mL (40.0 mmol) of 4 M NaOH [prepared from 1.65 g NaOH and 10 mL of water]. The solid dissolved to produce a biphasic mixture and the flask was cooled in a wet ice/methanol bath. From one dropping funnel was added dropwise 20 mL (140 mmol) of benzyl chloroformate over a 15 minute period, simultaneously from a second dropping funnel was added 100 mL (100 mmol) of 1 M NaOH (prepared from 4.00 g NaOH and 100 mL of water) to maintain basicity of the biphasic mixture. After complete addition, the flask was allowed to warm to room temperature and the mixture stirred for 72 hrs.

The mixture was transferred to a separatory funnel and the layers separated. The aqueous phase was extracted with DCM. The combined organic extracts were washed twice with saturated brine, dried over MgSO₄, and concentrated in vacuo. There was obtained 12.00 g (33.5 mmol, 93% yield) of product as a colorless oil which solidified upon storage at −20 C.

NP-HPLC: retention time=11.38 minutes(isocratic elution using 1:1 Hexane: DCM)

NMR (CDCl₃): 7.40 (s, $C_6\underline{H}_5$); 5.33 (s, N$\underline{H}$); 5.25 (s, O C$\underline{H}_2$C₆H₅); 2.50 (s, SC$\underline{H}_3$)

MS: M+H=359 by DCI; calculated (M+H)=359.4.

Example 29

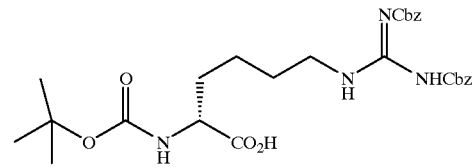

Boc-D-Har(Cbz)₂-OH:

A solution of 1.52 g (6.17 mmol) of Boc-D-Lys-OH, 2.33 g (6.53 mmol) of $N_1$, $N_2$-(Cbz)₂-S-methylisothiourea, 5.0 mL (28.7 mmol) of DIEA, and 45 mL of methanol was stirred at room temperature under a $N_2$ atmosphere for 21 hrs.

The colorless solution was acidified to pH=1 with 10% HCl and extracted twice with ethyl acetate. The combined organic extracts were washed once with saturated brine, dried over MgSO₄, and concentrated in vacuo. Under high vacuum, there was obtained 2.82 g (5.07 mmol, 82% yield) of product as a colorless, viscous gel.

RP-HPLC: retention time=13.76 minutes; $C_{18}$, 0-100% $CH_3CN$ over 25 minutes, 2.0 mL/min.

MS: M+H=557 by electrospray; calculated (M+H)= 557.6.

Example 30

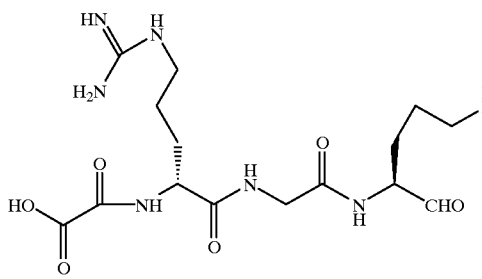

Oxaloyl-D-Arg-Gly-Arg-H

Oxaloyl-D-Arg-Gly-Arg-H was prepared via solid phase synthesis according to the procedure of Webb et al. The Boc-Arg(NO2)carbazone resin was prepared by loading $N_\alpha$-Boc($N_g$,NO2)argininal semicarbazonyl-$N_2$trans-4-methylenecyclohexane-1-carboxylic acid onto MBHA (methylbenzhydrylamine) resin (0.57 mmol/g) using the described procedure. Starting with 820 mg of Boc-Arg(NO2)-carbazone resin, sequential peptide elongation was as follows: (1) the resin is treated with 8 mL of 40% TFA/$CH_2Cl_2$ for 15 min. and washed 3 times with $CH_2Cl_2$, one time with 5% DIEA/$CH_2Cl_2$, and 3 times with $CH_2Cl_2$; (2) coupling with 148 mg of Boc-Gly, 113 mg of HOBt, 318 mg HBTU, 292 μL of DIEA in 10 mL DMF for 0.5 h; the resin is then washed once with DMF, 3 times with $CH_2Cl_2$, once with MeOH, and 3 times with $CH_2Cl_2$; (3) repeat step 1; (4) repeat step 2 using 229 mg of Boc-D-Arg(Cbz)$_2$OH instead of Boc-Gly; (5) repeat step 1; (6) repeat step 2 using 150 mg of monobenzyloxalate; (7) the resin is then washed once with DMF, 3 times with $CH_2Cl_2$, once with MeOH, and 3 times with $CH_2Cl_2$. The protected peptide aldehyde is cleaved by shaking, the resin, a solution of 5 mL of THF, 1 mL AcOH, 1 mL of 37% aqueous formaldehyde, and 0.1 mL of 1N HCl for 1 h. The filtrate is collected and the resin is washed with 2 mL each of THF, 50% aqueous THF, and water. The combined filtrates are diluted with 25 mL of water and extracted 3 times with EtOAc. The combined organic layers are washed with 5% NaHCO$_3$, 2 times with water, once with brine, dried (MgSO$_4$), and evaporated in vacuo to give 78 mg of an oil: RP-HPLC retention: 12.04, 12.53, and 12.44 min (tautomers). The oil in 2.5 mL of 10% aqueous MeOH containing 68 μAcOH and 50 mg of 5% palladium on charcoal (Degaussa, 50% water by weight) is placed on a Parr hydrogenator and shaken for 2.25–3.5 h at 30 psi. The solution is filtered and lyophilized to give 12.5 mg of a white solid.

RP-HPLC retention: 2.98 min; 3.47 min (thiosemicarbazone derivative); $C_{18}$, 0-100% $CH_3CN$ over 25 minutes, 2.0 mL/min.

MS: (M+H)=444.5 by fast atom bombardment, calculated (M+H)=444.2.

Example 31

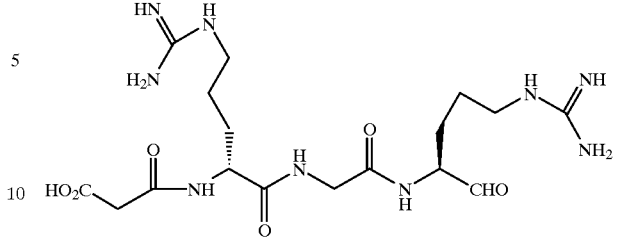

Malonoyl-D-Arg-Gly-Arg-H

Malonoyl-D-Arg-Gly-Arg-H was prepared via the solid phase method in Example 30 except that the growing peptide is capped with monobenzylmalonate. After lyophilization, a 40% yield of a white solid is obtained:

RP-HPLC retention: 2.98 min; 3.94 min (thiosemicarbazone derivative); $C_{18}$, 0-100% $CH_3CN$ over 25 minutes, 2.0 ml/min.

MS: (M+H)=458.3 by fast atom bombardment, calculated (M+H)=458.2.

Example 32

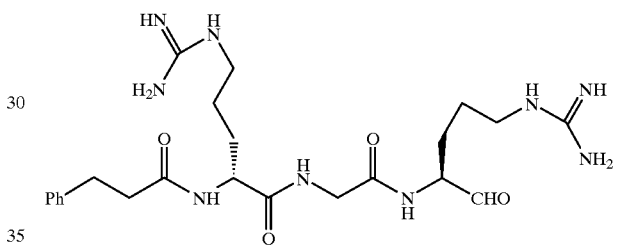

Ph(CH$_2$)$_2$CO-(D-Arg)-Gly-Arg-H

3-Phenylpropanoyl-D-Arg-Gly-Arg-H was prepared in a similar fashion via the solid phase method in Example 30 except that the growing peptide is capped with 3-phenylpropanoic adid. The crude product after hydrogenolysis and filtration is purified by preparative RP-HPLC (18 mL/min, 2.5×25 cm Vydac C-18) using a linear gradient of 100% water/0.1% TFA to 100% $CH_3CN$/0.1% TFA. The appropriate fractions are pooled and lyophilized to give a 57% yield of a white solid:

RP-HPLC retention: 8.65 min and 883 (tautomers); 8.87 min (thiosemicarbazone derivative); 11.02 min (2,4-dinitrophenylhydrazone derivative); $C_{18}$, 0-100% $CH_3CN$ over 25 minutes, 2.0 mL/min.

MS: (M+H)=504.3 by fast atom bombardment calculated (M+H)=504.3.

Example 33

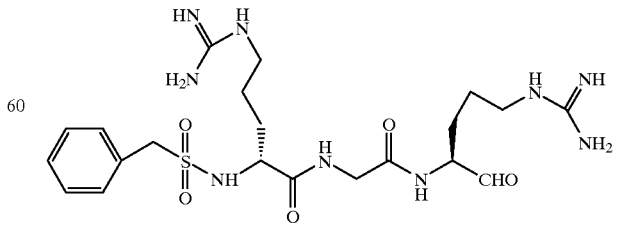

BnSO$_2$-D-Arg-Gly-Arg-H

Benzylsulfonyl-D-Arg-Gly-Arg-H was prepared in a similar fashion via the solid phase method in Example 30 except that the growing peptide is capped with benylsulfonyl chloride (6 eq) and DIEA (12 eq) in DCM. The crude, product after hydrogenolysis and filtration, is purified by preparative RP-HPLC (18 mL/min, 2.5×25 cm Vydac C-18) using a linear gradient of 100% water/0.1% TFA to 100% CH3CN/0.1% TFA. The appropriate fractions are pooled and lyophilized to give a 48% yield of a white solid:

RP-HPLC retention: 8.19 min and 8.51 (tautomers); 10.15 min (2,4-dinitrophenylhydrazone derivative); $C_{18}$, 0-100% $CH_3CN$ over 25 minutes, 2.0 mL/min.

MS: (M+H)=526.4 by fast atom bombardment, calculated (M+H)=526.3.

Example 34

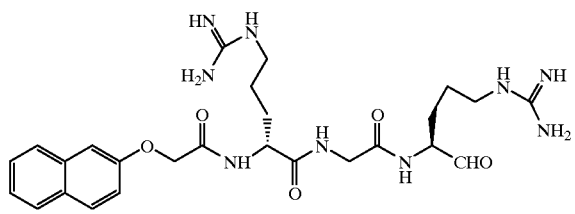

2-NapOCH$_2$CO-D-Arg-Gly-Arg-H

2-Napthoxyacetyl-D-Arg-Gty-Arg-H was prepared in a similar fashion via the solid phase method in Example 30 except that the arginine resin is protected as the bis-Cbz derivative made from the aldehyde of Example 27. The peptide was capped using (2-Naphthoxy)acetic acid N-hydroxysuccimide ester. The crude product after hydrogenolysis and filtration is purified by preparative RP-HPLC (18 mL/min, 2.5×25 cm Vydac C-18) using a linear gradient of 100% water/0.1% TFA to 100% $CH_3CN$/0.1% TFA. The appropriate fractions are pooled and lyophilized to give a 39% yield of a white solid:

RP-HPLC retention: 9.49 min and 9.74 (tautomers); 9.76 min (semicarbazone derivative); 11.57 min (2,4dinitrophenylhydrazone derivative); $C_{18}$, 0-100% $CH_3CN$ over 25 minutes, 2.0 mL/min.

MS: (M+H)=556.2 by fast atom bombardment, calculated (M+H)=556.4.

Example 35

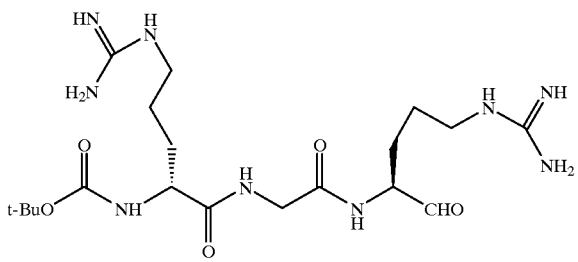

Boc-D-Cit-Gly-Arg-H

Boc-D-Cit-Gly-Arg-H was prepared in a similar fashion via the solid phase method in Example 30. The peptide was capped with Boc-D-Citrulline. After cdeavage and filtration from the resin, the filtrate is loaded directly onto a preparative RP-HPLC column (18 mL/min, 2.5×25 cm Vydac C-18) and eluted using a linear gradient of 100% water/0.1% TFA to 100% $CH_3CN$/0.1% TFA. The appropriate fractions are pooled and lyophilized to give the protected peptide. The crude product after hydrogenolysis and filration, is purified by preparative RP-HPLC (18 mL/min, 2.5×25 cm Vydac C-18) using a linear gradient of 100% water/0.1% TFA to 100% $CH_3CN$/0.1% TFA. The appropriate fractions are pooled and lyophilized to give a 3.8% yield of a white solid:

RP-HPLC retention: 10.94 min and 10.56 (tautomers); 12.96 min (thiosemicarbazone derivative); $C_{18}$, 0-100% $CH_3CN$ over 25 minutes, 2.0 mL/min.

MS: (M+H)=473.3 by fast atom bombardment, calculated (M+H)=473.4.

Example 36

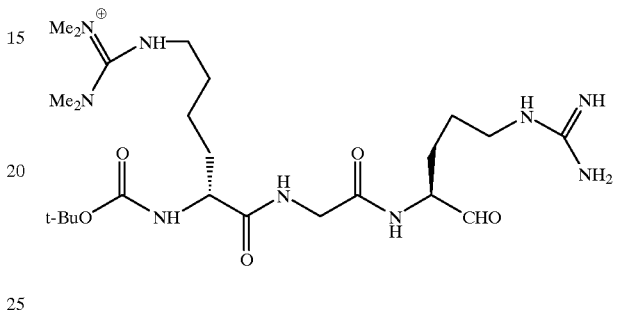

Boc-D-Har((CH$_3$)$_4$)-Gly-Arg-H

A 2.3 mg (3.6 μmol) sample of Boc-D-Lys-Gly-Arg-H, as prepared in Example 6, in 20 μL of DMF is added 3.3 mg (8.6 μmol) of HBTU followed by 1.6 μL (10.8 μmol) of DIEA. After 20 h at 23° C., the reaction mixture is loaded directly onto a RP-HPLC column (2 mL/min, 0.1×25 cm Vydac C-18) and eluted using a linear gradient of 100% water/0.1% TFA to 100% CH3CN/0.1% TFA. The appropriate fractions are pooled and lyophilized to give 1.6 mg (70%) of a white solid:

RP-HPLC retention: 9.44 and 9.96 min (tautomers); $C_{18}$, 0-100% $CH_3CN$ over 25 minutes, 2.0 mL/min.

MS: (M+H)=542.4 by fast atom bombardment, calculated (M+H)=542.4.

Example 37

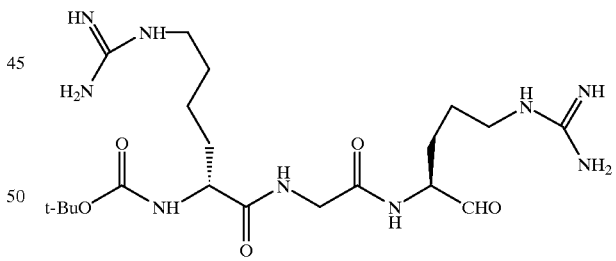

Boc-D-Har-Gly-Arg-H

Boc-D-Har-Gly-Arg-H was prepared in a similar fashion using the solid phase method of Example 30. The peptide was capped with Boc-Har-(Cbz$_2$)-OH, as prepared in Example 29. The crude product after hydrogenolysis for 5 h and filtration is lyophilized to give a 32% yield of a white solid:

RP-HPLC retention: 9.04 and 9.17 min (tautomers); 9.17 min (thiosemicarbazone derivative); 12.10 min (2,4dinitrophenylhydrazone derivative); $C_{18}$, 0-100% $CH_3CN$ over 25 minutes, 2.0 mL/min.

MS: (M+H)=486.3 by fast atom bombardment, calculated (M+H)=486.4.

Example 38

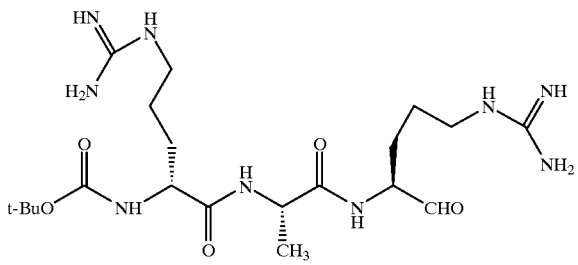

Boc-D-Arg-Ala-Arg-H

Boc-D-Arg-Ala-Arg-H was prepared in a similar fashion via the solid phase method in Example 34 except that the growing peptide is coupled with BocAlanine instead of Boc-Glycine. The crude product after hydrogenolysis and filtration is purified by preparative RP-HPLC (18 mumin, 2.5×26 cm Vydac C18) using a linear gradient of 100% water/0.1% TFA to 100% $CH_3CN$/0.1% TFA. The appropriate fractions are pooled and lyophilized to give a 15% yield of a white solid:

RP-HPLC retention: 11.24 min and 11.37 (tautomers); 16.88 min (2,4-dinitrophenylhydrazone derivative); C18, 0-100% CH3CN over 25 minutes, 2.0 mL/min. MS: (M+H)=486.3 by fast atom bombardment calculated (M+H)=486.3.

Example 39

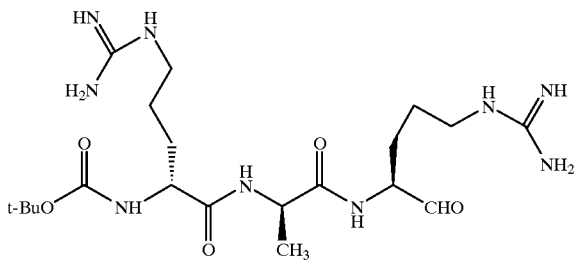

Boc-D-Arg-D-Ala-Arg-H

Boc-D-Arg-D-Ala-Arg-H was prepared in a similar fashion via the solid phase method in Example 34. The crude product after hydrogenolysis and filtration is lyophilized to give a white solid:

RP-HPLC retention: 11.53 min and 12.00 (tautomers); 11.71 min (thiosemicarbazone derivative); 16.83 min (2,4dinitrophenylhydrazone derivative); $C_{18}$, 0-100% $CH_3CN$ over 25 minutes, 2.0 mL/min.

MS: (M+H)=486.2 by fast atom bombardment calculated (M+H)=488.3.

Example 40

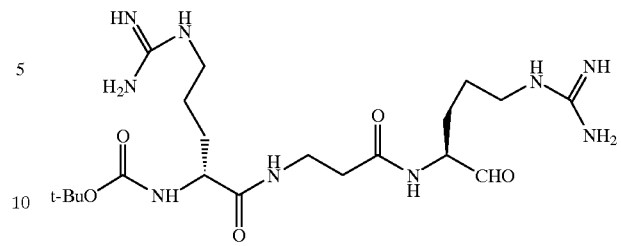

Boc-D-Arg-β-Ala-Arg-H

Boc-D-Arg-β-Ala-Arg-H was prepared in a similar fashion using the solid phase method in Example 34. The crude product after hydrogenolysis and filtration is purified by preparative RP-HPLC (18 mL/min, 2.5×25 cm Vydac C-18) using a linear gradient of 100% water/0.1% TFA to 100% CH3CN/0.1% TFA. The appropriate fractions are pooled and lyophilized to give a 52% yield of a white solid:

RP-HPLC retention: 11.48 min and 11.73 min (tautomers); 11.42 min (thiosemicarbazone derivative); 16.80 min (2,4-dinitrophenylhydrazone derivative); $C_{18}$, 0-100% $CH_3CN$ over 25 minutes, 2.0 mL/min.

MS: (M+H)=486.3 by fast atom bombardment, calculated (M+H)=488.3.

Example 41

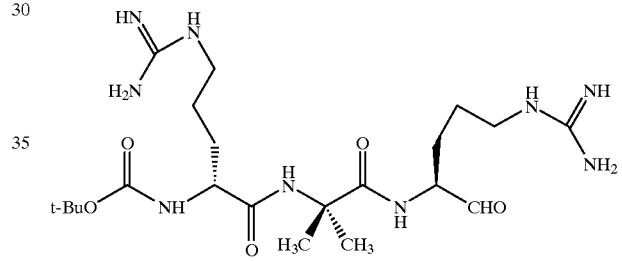

Boc-D-Arg-Aib-Arg-H

Boc-D-Arg-Aib-Arg-H was prepared in a similar fashion using the solid phase method in Example 34 except that the growing peptide is coupled with Boc-α-methylalanine instead of Boc-Gly and HATU is used as the coupling agent. The crude product after hydrogenolysis and filtration is purified by preparative RP-HPLC (18 mL/min, 2.5×25 cm Vydac C-18) using a linear gradient of 100% water/0.1% TFA to 100% CH3CN/0.1% TFA. The appropriate fractions are pooled and lyophilized to give a 23% yield of a white solid:

RP-HPLC retention: 11.84, 12.07 and 12.19 min (tautomers); 16.91 min (2,4dinitrophenylhydrazone derivative); $C_{18}$, 0-100% $CH_3CN$ over 25 minutes, 2.0 mL/min.

MS: (M+H)=500.2 by fast atom bombardment, calculated (M+H)=500.3.

Example 42

Boc-D-Arg(NO$_2$)(OH)CONHEtPh

To a solution of Boc-Arg(NO$_2$)(OH)COOH, prepared by the method of Webb, T. R. et al, Patent No. WO 94/08941 (Oct. 18, 1993), (850 mg, 2.4 mmol) and phenethylamine (609 uL, 4.8 mmol) in 10 mL DMF is added BOP (1.3 g, 2.9 mmol) followed by DIEA (630 uL 3.6 mmol). The solution was allowed to stir for 18h. The reaction mixture was dissolved in EtOAc (250 mL) and washed with 1N HCl (75 mL), H₂O (75 mL), 5% NaHCO₃ (75 mL) and brine (75 mL). The organic layer was dried over MgSO₄ and concentrated in vacuo to afford 900 mg (82%) of a light brown solid.

RP-HPLC: 15.30, 15.95 min.; $C_{18}$, 0–100% $CH_3CN$ over 25 min., 1.5 mL/min.

MS:(M+H)=453.2 by electrospray; calculated (M+H)= 453.8.

Example 43

Boc-D-Arg(NO₂)(OH)CONHBn

Boc-Arg(NO₂)(OH)CONHBn was prepared according to Example 42 by coupling benzylamine to Boc-Arg(NO₂)(OH)COOH in a 81% yield.

RP-HPLC:14.6, 15.2 min.; $C_{18}$, 0–100% $CH_3CN$ over 25 min., 1.5 mL/min.

MS:(M+H)=439:0 by electrospray; calculated (M+H)= 439.4.

Example 44

Boc-D-Arg(NO₂)(OH)CON(CH₂)₄

Boc-Arg(NO₂)(OH)CON(CH₂)₄ was prepared according to Example 42 by coupling pyrollidine to Boo-Arg(NO₂)(OH)COOH in a 44% yield.

RP-HPLC: 13.0, 13.1 min.; $C_{18}$, 0–100% $CH_3CN$ over 25 min., 1.5 mL/min.

MS:(M+H)=303.0 by electrospray (boc group removed in the spectrometer); calculated (M+H))=403.4.

Example 45

Boc-D-Arg(Cbz)₂-Gly-OH

Bac-D-Arg(Cbz)₂OH (Bachem) was coupled to glycine according to Example 1 in quantitative yield as a white foam.

RP-HPLC: 18.9 min.; $C_{18}$, 0–100% $CH_3CN$ over 25 min., 1.5 mL/min.

Example 46

BnSO₂-D-Arg(Tos)-Gly-OH

To a solution of Boc-D-Arg(Tos)OH (11.2 g, 26.1 mmol), HOBt (3.9 g, 28.7 g), glycine benzyl ester hydrochloride (5.2 g, 26.1 mmol) in 52 mL of DCM is added DIEA (4.5 mL, 26.1 mmol) followed by DCC (5.9 g, 28.7 mmol; dissolved in 5 mL of DCM). After stirring for 18 h, the reaction mixture is cooled to −10° C. and the precipitate is filtered off. The filtrate is extracted twice with 1N Hcl (50 mL), twice with 5% NaHCO₃ (50 mL), brine (50 mL), dried (MgSO₄), and concentrated in vacuo to give 15.2 g (100%) of Boc-D-Arg(Tos)Gly-Gly-OBn as a white solid. RP-HPLC: 18.9 min.; $C_{18}$, 0–100% $CH_3CN$ over 25 min., 1.5 mL/min.

To a solution of D-Arg(Tos)-Gly-OBn (5.2 mmol; Boc previously removed by treatment with 40% TFA/DCM (0.1M) for 15 min. and then concentrated in vacuo; RP-HPLC: 13.8 min.; $C_{18}$, 0–100% $CH_3CN$ over 25 min., 1.5 mL/min) in 21 mL of DCM is neutralized with DIEA before cooling to −78° C. where 1.19 g (6.24 mmol) of BnSO₂Cl is added as a solid followed by 900 uL (10.4 mmol). The solution is allowed to warm to 23° C. and stirr for 18 h. The eaction mixture was extracted twice with 10% citric acid, twice with 5% NaHCO₃ (50 mL), brine (50 mL), dried (MgSO₄), and concentrated in vacuo to give 3.2 g (97%) of BnSO₂-D-Arg(Tos)Gly-OBn as a white solid. RP-HPLC: 18.0 min.; $C_{18}$, 0–100% $CH_3CN$ over 25 min., 1.5 mL/min.

The benzyl ester is removed by hydrogenation of 3.2 g of BnSO₂-D-Arg(Tos)Gly-OBn dissolved in 50 mL of MeOH with 800 mg of 5%Pd/C (50% wt. water), and 50 psi pressure of hydrogen on a Parr apparatus for 1.5 h. The mixture is filtered through celite and concentrated in vacuo to give 2.54 g (93%) of the title compound as a white foam.

RP-HPLC: 15.0 min.; $C_{18}$, 0–100% $CH_3CN$ over 25 min., 1.5 mL/min.

Example 47

Boc-D-Arg(Cbz)₂-Gly-Arg(NO₂)(OH)COOH

To a solution of 2.85 mg (4.75 mmol) of Boc-D-Arg(Cbz)₂-Gly-OH and 0.66 g (5.7 mmol) of N-hydroxysuccinimide dissolved in 9.5 mL dioxane was added a solution of 1.08 g (5.23 mmol) of DCC dissolved in 4.0 mL of dioxane. The resultant solution was stirred at room temperature for 18 h, during which time the DCU separated from the solution. The solids were removed by vacuum filtration and the clear colorless filtrate was treated with a single portion of Arg(NO₂)(OH)COOH (1.658 g, 4.74 mmol, the Boc was previously removed with 40% TFA/DCM (0.1M) for 30 min, and concentrated in vacuo) and sodium bicarbonate (1.2 g, 14.22 mmol) dissolved in 8.5 mL of water. The resultant mixture was stirred at room temperature 18 h. The solution was acidified to pH 1–2 with 10% HCl solution and extracted with ethyl acetate three times. The combined organics were washed twice with brine, dried over MgSO₄, and concentrated in vacuo to afford 2.4 g (54%) of a light brown solid.

RP-HPLC: 17.90 min; $C_{18}$, 0–100% $CH_3CN$ over 25 min., 1.5 mL/min.

MS:(M+H)=831.0; calculated (M+H)=831.35.

Example 48

Boc-D-Arg(Cbz-Gly-Arg(NO₂)(OH)CONHCH₃

To a solution of Boc-D-Arg(Cbz)₂-Gly-Arg(NO₂)(OH)COOH (200 mg, 0.22 mmol) and methylamine (9 uL, 0.24 mmol) in 1 mL DMF, is added BOP (0.11 g, 0.26 mmol) followed by NMM (70 uL, 0.65 mmol). The solution was allowed to stir 18 h. The reaction mixture was dissolved in EtOAc (25 mL) and washed with 1N HCl (5 mL), Water (5 mL), 5% NaHCO₃(5 mL) and brine (5 mL). The organic layer was dried over MgSO₄ and concentrated in vacuo to afford 145 mg (72%) as a light brown solid.

RP-HPLC: 17.80 min.; $C_{18}$, 0–100% $CH_3CN$ over 25 min., 1.5 mL/min.

MS:(M+H)=844.5; calculated (M+H)=844.41.

Example 49

Boc-D-Arg(Cbz)₂-Gly-Arg(NO₂)(OH)CONHPh

Boc-D-Arg(Cbz)₂-Arg(NO₂)(OH)CONHPh was prepared according to Example 48 by couplig aniline to Boc-D-Arg(Cbz)₂-Gly-Arg(NO₂)(OH)COOH in a 80% yield.

RP-HPLC: 20.0 min.; $C_{18}$, 0–100% $CH_3CN$ over 25 min. 1.5 mL/min.

MS:(M+H)=906.6 by ealsctospray; calculated (M+H)= 906.5.

Example 50

Boc-D-Arg(Cbz)₂-Gly-Arg(NO₂)(OH)CONHEtPh

To a solution of Boc-D-Arg(Cbz)₂-Gly-OH (771 mg, 1.29 mmol) in 5 mL of DMF was added a solution of Arg(NO₂)(OH)CONHEtPh, (Boc was previously removed with 40% TFA/DCM (0.1M) for 30 min, and dried in vacuo in DMF (2.15 mL, reaction conc 0.2M) and BOP (695 mg, 1.57 mmol) followed by DIEA (746 uL, 4.29 mmol). The solution was allowed to stir 18h. The reaction mixture was dissolved in EtOAc (250 mL) and washed with 1N HCl (75 mL), H₂O (75 mL), 5% NaHCO₃ (75 mL) and brine (75 mL). The organic layer was dried over MgSO₄ and concentrated in vacuo to afford 1.19 g (89%) as an off white solid.

RP-HPLC: 19.40 min.; $C_{18}$, 0–100% $CH_3CN$ over 25 min., 1.5 mL/min.

MS:(M+H)=934.3; calculated (M+H)=934.3.

Example 51
$BnSO_2$-D-Arg(Cbz)$_2$-Gly-Arg(NO$_2$)(OH)CONHEtPh

To a 0° C. solution of D-Arg(Cbz)$_2$-Gly-Arg(NO$_2$)(OH) CONHEtPh (990 mg, 1.1 mmol; Boc was previously removed with 40%TFA/DCM (0.1M) for 30 min, and concentrated in vacuo) in DCM (4.24 mL) and DIEA (555 uL, 3.3 mmol) was added $BnSO_2Cl$ (222 mg, 1.2 mmol). The solution was allowed to stir 18 h after which the reaction mixture was dissolved in EtOAc (250 mL) and washed with 1N HCl (75 mL), $H_2O$ (75 mL), 5% NaHCO3 (75 mL) and brine (75 mL). The organic layer was dried over $MgSO_4$ and concentrated in vacuo to afford 440 g (42%) as an off-white solid.

RP-HPLC: 19.79 min. $C_{18}$, 0–100% $CH_3CN$ over 25 min., 1.5 mL/min.

MS:(M+H)=988.4; calculated (M+H)=988.1.

Example 52
$BnSO_2$-D-Arg-Gly-Arg-CONHEtPh

To $BnSO_2$-D-Arg(Cbz)$_2$-Gly-Arg(NO$_2$)(OH)CONHEtPh (200 mg, 0.202 mmol) was added Anisole (1 mL), ethylmethylsulfide (0.5 mL), and HF (20 mL anhydrous). The reaction was allowed to stir for 1.5h at 0° C. The HF was removed in vacuo and the reaction mixture washed 3 times with chilled ether, glacial acetic acid, and water. The aqueous wash was lyophilized directly and 100 mg (0.148 mmol) of this crude material redissolved in 1M TFA in DMSO (222 uL, 1.5 eq) and IBX (1.48 mL, 0.5M in DMSO). The reaction is allowed to stir 18 h. The reaction mixture is purified directly on a 5.0 cm $C_{18}$ column and lyophilized directly to give 74.1 mg (74%) as a fluffy white solid.

RP-HPLC: 12.96 min.; $C_{18}$, 0–100% $CH_3CN$ over 25 min., 1.5 mL/min.

MS:(M+H)=673.2; calculated (M+H)=673.3.

Example 53
Boc-D-Arg(Cbz)$_2$-Gly-Arg(NO$_2$)CONHEtPh

To a solution of Boc-D-Arg(Cbz)$_2$-Gly-Arg(NO$_2$)(OH) CONHEtPh (275 mg, 0.294 mmol in DMSO/Toluene(1:1) (6 mL) was added EDC (731 mg, 3.8 mmol) and DCA (97 uL, 1.18 mmol). The reaction was allowed to stir for 18 h. The reaction was purified directly by flash silica gel chromatography(10% MeOH/DCM/0.1% AcOH) to yield 190 mg (89%) of a white solid.

RP-HPLC: 19.27 min.(2 peaks); $C_{18}$, 0–100% $CH_3CN$ over 25 min., 1.5 mL/min.

MS:(M+H)=932.5; calculated (M+H)=932.28.

Example 54
Boc-D-Arg-Gly-Arg-CONHEtPh

To a solution of Boc-Arg(Cbz)$_2$-Gly-Arg(NO$_2$) CONHEtPh (190 mg, 0.204 mmol) in MeOH (15.4 mL) was added 10% Pd/C (153 mg, 70 mol %) and 1N HCl (402 uL) and $H_2$ at 50 psi. The reaction was allowed shake for 8 h. The catalyst was removed by filtration through celite and the reaction mixture diluted with water and lyophilized. The crude solid was redissolved in water and purified directly on a 2.5 cm×25 cm $C_{18}$ column (0–60% ACN/0.1% TFA) to yield 42 mg (33%) of a white solid.

RP-HPLC: 13.44 min.; $C_{18}$, 0–100% $CH_3CN$ over 25 min., 1.5 mL/min.

MS:(M+H)=619.3; calculated (M+H)=619.3.

Example 54
D-Arg-Gly-Arg-CONHEtPh

To Boc-D-Arg-Gly-ArgCONHEtPh (2.3 mg, 0.004 mmol) was added 40%TFA/DCM (0.1M) for 30 min, and dried in vacuc.

RP-HPLC: 11.77 min. $C_{18}$, 0–100% $CH_3CN$ over 25 min., 1.5 mL/min.

MS:(M+H)=519.0; calculated (M+H)=519.3.

Example 56
Boc-D-Arg(Cbz)$_2$-Gly-Arg(NO$_2$)(OH)CONHBn

Boc-D-Arg(Cbz)$_2$-Gly-Arg(NO$_2$)(OH)CONHBn was prepared according to Example 47 by coupling Arg-(NO$_2$) (OH)CONHBn to Boc-D-Arg(Cbz)$_2$Gly-OH in a 60% yield.

RP-HPLC: 19.32 min.; $C_{18}$, 0–100% $CH_3CN$ over 25 min., 1.5 mL/min.

MS:(M+H)=920.5 by electrospray; calculated (M+H)=921.0.

Example 57
Boc-D-Arg(Cbz)$_2$-Gly-Arg-(NO$_2$)(OH)CON(CH$_2$)$_4$

Boc-D-Arg(Cbz)$_2$ -Gly-Arg(NO$_2$)(OH)CON(CH$_2$), was prepared according to Example 50 by coupling Arg-(NO$_2$) (OH)CON(CH$_2$)$_4$ to Boc-D-Arg(Cbz)$_2$-Gly-OH. The crude organic layer, after workup, was purified by flash silica gel chromatography (8% MeOH/DCM/0.1% AcOH) to yield 117 mg (59%) of a white solid.

RP-HPLC: 17.96 min.; $C_{18}$, 0–100% $CH_3CN$ over 25 min., 1.5 mL/min.

MS:(M+H)=884.5 electrospray; calculated (M+H)=883.98.

Example 58
$BnSO_2$-D-Arg(Cbz)$_2$-Gly-Arg(NO$_2$)(OH)CON(CH$_2$)$_4$ $BnSO_2$-D-Arg(Cbz)$_2$-Gly-Arg(NO$_2$)(OH)CON(CH$_2$)$_4$ was prepared according to Example 51. The reaction mixture was purified directy by flash silica gel chromatography (10%MeOH/DCM/0.1% AcOH) to yield 35 mg (37%).

RP-HPLC: 18.12 min.; $C_{18}$, 0–100% $CH_3CN$ over 25 min., 1.5 mL/min.

Example 59
$BnSO_2$-D-Arg-Gly-Arg-CON(CH$_2$)$_4$ $BnSO_2$-D-Arg-Gly-ArgCON(CH$_2$), was prepared according to Example 52 to yield 2.3 mg (14%).

RP-HPLC: 12.09 $C_{18}$, 0–100% $CH_3CN$ over 25 min., 1.5 mL/min.

MS:(M+H)=623.2 electrospray; calculated (M+H)=623.3.

Example 60
Boc-D-Arg(Cbz)$_2$-Gly-Arg(NO$_2$)CONHBn

Boc-D-Arg(Cbz)$_2$-Gly-Arg(NO$_2$)(OH)CONHBn was prepared according to Example 53. The reaction mixture was purified directly by flash silica gel chromatography (10%MeOH/DCM/0.1% AcOH) to yield 48.5 mg (32%).

RP-HPLC: 19.80 (2 peaks); $C_{18}$, 0–100% $CH_3CN$ over 25 min., 1.5 mL/min.

MS:(M+H)=918.4 by electrospray; calculated (M+H)=918.81.

Example 61
Boc-D-Arg-Gly-Arg-CONHBn

Boc-D-Arg(Cbz)$_2$-Gly-Arg(NO$_2$)(OH)CONHBn was oxidized and purified as in Example 53 followed by hydrogentation and purification as in Example 13 to yield 5 mg (17%).

RP-HPLC: 13.76 broad peak; $C_{18}$, 0–100% $CH_3CN$ over 25 min., 1.5 mL/min.

MS:(M+H)=605.5 electrospray; calculated (M+H)= 605.7.

Example 62
Boc-D-Arg(Cbz)$_2$-Gly-Arg(NO$_2$)CONHCH$_3$

Boc-D-Arg(Cbz)$_2$-Gly-Arg(NO$_2$)(OH)CONHCH$_3$ was prepared according to Example 53. The reaction mixture was diluted with EtOAc and washed with water, brine, and dried over MgSO$_4$ to yield 47 mg (39%).

RP-HPLC: 17.85(2 peaks) C$_{18}$, 0–100% CH$_3$CN over 25 min., 1.5 mL/min.

Example 63
Boc-D-Arg-Gly-Arg-CONHCH$_3$

Boc-Arg-Gly-Arg-CONHCH$_3$ was prepared according to Example 54 to yield 5 mg (17%).

RP-HPLC: 13.76 broad peak C$_{18}$, 0–100% CH$_3$CN over 25 min., 1.5 mL/min.

MS:(M+H)=529.0 electrospray; calculated (M+H)= 529.32.

Example 64
Boc-D-Arg(Cbz)$_2$-Gly-Arg(NO$_2$)CONHPh

Boc-D-Arg(Cbz)$_2$-Gly-Arg(NO$_2$)(OH)CONHPh was oxidized according to Example 53. The reaction rnxture was diluted with EtOAc and washed with water, brine, and dried over MgSO$_4$ to yield 96 mg (96%) of a white foam.

RP-HPLC: 20.0; C$_{18}$, 0–100% CH$_3$CN over 25 min., 1.5 mL/min.

MS:(M+H)=904.5.0 by electrospray; calculated (M+H)= 904.3.

Example 65
D-Arg-Gly-Arg-CONHPh

Boc-D-Arg(Cbz)$_2$-Gly-Arg(NO$_2$)CONHPh was submitted to the HF cleavage conditions of Example 11 to yield 2 mg (18.4%) of a white solid.

RP-HPLC: 11.42 broad peak C$_{18}$, 0–100% CH$_3$CN over 25 min., 1.5 mL/min.

MS:(M+H)=491.0 electrospray; calculated (M+H)= 491.6.

Example 66
Boc-D-Arg(Tos)-Gly-Arg(NO$_2$)(OH)CONBn

The titled compound was prepared according to Example 50 by coupling Arg-(NO$_2$)(OH)CONHBn to BnSO$_2$-D-Arg (Tos)-Gly-OH except that apon dilution of the organic layer and addition of 1N HCl, a oily precipitate is formed which is collected and re-precipitated with MEOH and water. The solid is collected, redissolved in MEOH and lyophilized to-give a 38% yield of a white solid.

RP-HPLC: 15.9 min.;C$_{18}$, 0–100% CH$_3$CN over 25 min., 1.5 mL/min.

Example 67
BnSO$_2$-D-Arg-Gly-Arg-CONBn

BnSO$_2$-D-Arg-Gly-ArgConBn was prepared according to Example 52 to yield 110 mg (73%) of a fluffy white solid.

RP-HPLC: 11.6 min (broad peak) C$_{18}$, 0–100% CH$_3$CN over 25 min., 1.5 mL/min. MS:(M+H)=659.2 electrospray; calculated (M+H)=659.3.

Example 68

Evaluation of the compounds of this invention is guided by in vitro protease activity assays (see below) and in vivo studies to evaluate biological half-life, antithrombotic efficacy, and effects on hemostasis and hematological parameters (see Example 69 below).

The compounds of the present Invention are dissolved in buffer to give solutions containing concentrations such that assay concentrations range from 0 to 100 $\mu$M. In the assays for thrombin, prothrombinase and factor Xa, a synthetic chromogenic substrate is added to a solution containing test compound and the enzyme of interest and the residual catalytic activity of that enzyme is determined spectrophotometrically. The IC$_{50}$ of a compound is determined from the substrate turnover. The IC$_{50}$ is the concentration of test compound giving 50% inhibition of the substrate turnover. The compounds of the present invention desirably have an IC$_{50}$ of less than 500 nM in the factor Xa assay, preferably less than 200 nM, and more preferred compounds have an IC$_{50}$ of about 100 nM or less in the factor Xa assay. The compounds of the present invention desirably have an IC$_{50}$ of less than 4.0 $\mu$M in the prothrombinase assay, preferably less than 200 nM, and more preferred compounds have an IC$_{50}$ of about 10 nM or less in the prothrombinase assay. The compounds of the present invention desirably have an IC$_{50}$ of greater than 1.0 $\mu$M in the thrombin assay, preferably greater than 10.0 $\mu$M, and more preferred compounds have an IC$_{50}$ of greater than 100.0 $\mu$M in the thrombin assay.

Amidolytic Assays for determining protease inhibition activity

The factor Xa and thrombin assays were performed at room temperature, in 0.02 M Tris-HCl buffer, pH 7.5, containing 0.15 M NaCl. The rates of hydrolysis of the para-nitroanilide substrate S2765 (Chromogenix) for factor Xa, and the substrate Chromozym TH (Boehringer Mannhelm) for thrombin following preincubation of the enzyme with inhibitor for 5 minutes at room temperature, and were determined using the Softmax 96-well plate reader (Molecular Devices), monitored at 405 nm to measure the time dependent appearance of p-nitroaniline.

The prothrombinase inhibition assay was performed in a plasma free system with modifications to the method described by Sinha, U. et al., Thromb. Res., 75, 427–436 (1994). Specifically, the activity of the prothrombinase complex was determined by measuring the time course of thrombin generation using the p-nitroanilide substrate Chromozym TH. The assay consists of preincubation ( 5 minutes) of selected compounds to be tested as inhibitors with the complex formed from factor Xa (0.5 nM), factor Va (2 nM), phosphatidyl serine:phosphatidyl choline (25:75, 20 $\mu$M) in 20 mM Tris HCl buffer, pH 7.5, containing 0.15 M NaCl, 5 mM CaCl$_2$ and 0.1% bovine serum albumin. Aliquots from the complex-inhibitor mixture were added to prothrombin (1 nM) and Chromozym TH (0.1 mM). The rate of substrate cleavage was monitored at 405 nm for two minutes. Eight different concentrations of inhibitor were assayed in duplicate. A standard curve of thrombin generation by an equivalent amount of untreated complex was used for determination of percent inhibition.

Example 69

A series of studies were accomplished in rabbits to evaluate the biological half-life, antithrombotic efficacy, and effects on hemostasis and hematological parameters of the compound Boc-D-Arg-Gly-Arg-H (referred to in this example as "Boc-RGR-H").

Pharmacokinetics/Pharmacodynamics

Rabbits were anesthetized with intramuscular (I.M.) injections of Ketamine, Xylazine, and Acepromazine cocktail. A marginal ear vein and femoral vein were cannulated for drug administration and blood sampling. Citrated blood samples were obtained serially for two hours after intravenous (I.V.) bolus injection of Boc-RGR-H (2.0 mg/kg).

Coagulation parameters [Activated Partial Thromboplastin times (aPTT), Prothrombin times (PT), and Fibrinogen (FIB)] and hematological parameters [red blood cell (RBC), white blood cell (WBC), hematocrit (HcT), and platelet (PLT) counts] were measured on samples obtained at designated time points. Plasma concentrations of Boc-RGR-H were determined by HPLC.

Pk/Pd Results

Boc-RGR-H (2.0 mg/kg) exhibited a plasma concentration-dependent anticoagulative effect. The peak plasma concentration by HPLC was 3.78 µg/mL. This dose of Boc-RGR-H generated a 2.45 fold aPTT prolongation as compared to pretreatment values. The PT value was also prolonged by 1.15 fold and FIB were slightly prolonged 1.07 fold. There were no significant changes in hematological parameters as compared to saline controls.

Following I.V. administration, Boc-RGR-H was cleared from the plasma in a monoexponential decay (one-compartment model). The mean plasma half-life of Boc-RGR-H in rabbits was 70.6 minutes (n=3). The mean clearance value (CL) was 1.16 mL/min/kg with a volume of distribution of 118.3 mL/kg. Dosing rate for infusion studies was determined by {Dosing rate=CL×Css} where CL is clearance and Css is plasma concentration at steady state.

Antithrombotic Efficacy in a Rabbit Model of Venous Thrombosis

A rabbit deep vein thrombosis model as described by Hollenbach, S. at al., Thromb. Haemost 71, 357–362 (1994), was used to determine the in-vivo antithrombotic activity of the test compounds. Rabbits were anesthetized with I.M. injections of Ketamine, Xylazine, and Acepromazine cocktail. A standardized protocol consisted of insertion of a thrombogenic cotton thread and copper wire apparatus into the abdominal vena cava of the anesthetized rabbit. A non-occlusive thrombus was allowed to develop in the central venous circulation and inhibition of thrombus growth was used as a measure of the antithrombotic activity of the studied compounds. Test agents or control saline were administered through a marginal ear vein catheter. A femoral vein catheter was used for blood sampling prior to and during steady state infusion of test compound. Initiation of thrombus formation begins immediately after advancement of the cotton thread apparatus into the central venous circulation. Test compounds were administered from time= 30 min to time=150 min at which the experiment was terminated. The rabbits were euthanized and the thrombus excised by surgical dissection and characterized by weight and histology. Blood samples were analyzed for plasma concentrations and changes in hematological and coagulation parameters.

Effects of Boc-RGR-H in Rabbit Venous Thrombosis model

Administration of Boc-RGR-H in the rabbit venous thrombosis model demonstrated antithrombotic efficacy at the higher doses evaluated. There was a dose-dependent effect of the compound on the aPTT and PT prolongation with the highest dose (1500 µg/kg+14.85 µg/kg/min) extending aPTT and PT, 1.61 and 1.08 fold respectively (see Table 2). Boc-RGR-H had no significant effects on hematological parameters as compared to saline controls (see Table 3).

TABLE 2

ANTITHROMBOTIC EFFECTS OF Boc-RGR-H IN RABBITS

| Dose Regimen (µg/kg + µg/kg/min) | n# | % Inhibition of Thrombosis | fold increase over baseline aPTT | PT |
|---|---|---|---|---|
| saline control | 7 | 0.0 | 1.00 ± 0.05 | 1.01 ± 0.00 |
| 200 + 1.98 | 5 | 8.4 | 1.04 ± 0.05 | 1.02 ± 0.01 |
| 600 + 5.94 | 5 | −6.6 | 1.15 ± 0.02 | 1.03 ± 0.01 |
| 1000 + 9.90 | 5 | 58.6 | 1.31 ± 0.04 | 1.06 ± 0.01 |
| 1500 + 14.85 | 5 | 31.4 | 1.61 ± 0.13 | 1.08 ± 0.01 |

All measurements are an average of all samples after steady state administration of vehicle or Boc-RGR-H. Values are expressed as mean±SD.

TABLE 3

EFFECTS OF Boc-RGR-H ON HEMATOLOGICAL PARAMETERS

| Dose Regimen (µg/kg + µg/kg/min) | n# | RBC × $10^6/\mu L$ | WBC × $10^3/\mu L$ | PLT × $10^3/\mu L$ | Hct % |
|---|---|---|---|---|---|
| saline control | 7 | 5.64 ± 0.49 | 4.30 ± 1.63 | 432 ± 129 | 35.2 ± 2.81 |
| 200 + 1.98 | 5 | 5.69 ± 0.14 | 4.45 ± 0.97 | 393 ± 84 | 36.9 ± 3.90 |
| 600 + 5.94 | 5 | 5.74 ± 0.48 | 3.87 ± 0.65 | 442 ± 81 | 35.3 ± 3.01 |
| 1000 + 9.90 | 5 | 5.71 ± 0.28 | 5.09 ± 1.61 | 375 ± 73 | 35.5 ± 1.01 |
| 1500 + 14.85 | 5 | 5.80 ± 0.50 | 4.82 ± 1.01 | 433 ± 22 | 36.0 ± 3.31 |

All measurements are an average of samples after steady state administration of vehicle or Boc-RGR-H. Values are mean±SD.

Effects of Boc-RGR-H on Cuticle Bleeding times in Rabbits

In an ancillary study, a Cuticle Bleeding Time model was used to evaluate the effect of test compounds on bleeding time (BT) measurements in rabbits. The standardized protocol involved anesthesia and catheterization of rabbits as previously described in this Example 43. To measure BT, a toe nail was cut 5 mm from the base of the cuticle with a canine nail trimming device. Time until cessation of bleeding was recorded by wicking the blood on to BT blotting paper in 30 second intervals. Test compound was administered as a bolus followed by infusion regimen. Two BT measurements were obtained prior to administration of test compound and three BT measurements accomplished serially after initiation of steady state infusion of test compound. BT measurements were allowed to continue for up to 30 minutes at which time it was stopped with application of silver nitrate. Blood samples were obtained just prior to all BT measurements and processed for measurement of hematological and coagulation parameters.

The effect of Boc-RGR-H on rabbit cuticle BT at a dose of 1500 µg/kg+14.85 µg/kg/min was a increase of 2.14 fold (±1.26, n=4) from pre-administration baseline measurements. In these experiments average increase in aPTT and PT was 1.61 and 1.07 fold respectively. There were no significant changes in hematological parameters from pre to post Boc-RGR-H administration.

Although the invention has been described with reference to the disclosed embodiments, those skilled in the art will readily appreciate that the specific experiments detailed are only illustrative of the invention. It should be understood that various modifications can be made without departing from the spirit of the invention. Accordingly, the invention is limited only by the following claims.

What is claimed is:

1. A compound represented by the formula:

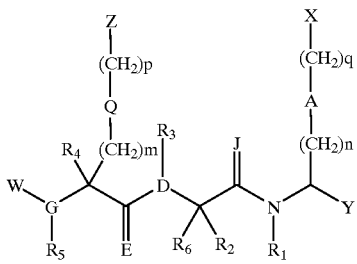

wherein:
m=0,1,2,3,4;
n=0,1,2,3,4;
p=0,1,2,3,4;
q=0,1,2,3,4;
Y=CHO, $COCF_3$, $COCF_2CF_3$, $COCO_2R_7$, $COCONR_8R_9$, $B(OR_{10})_2$; where: $R_7$, $R_8$, $R_9$, $R_{10}$ are the same or different and =H, $C_{1-6}$alkyl, $C_{3-8}$cycloalkyl, aryl$C_{1-3}$alkyl, heteroaryl$C_{1-3}$alkyl;
A=piperdinyl, pyrrolidinyl, cyclopropyl, cyclobutyl, cyclopentyl, cyclohexyl, phenyl, $C_{3-6}$heteroaryl, or is absent;
$R_1$=H or $C_{1-3}$alkyl;
J=O or $H_2$;
$R_2$=H or $C_{1-3}$alkyl;
D=N,CH, $NCH_2$, $NCH_2CH_2$, $CHCH_2$;
$R_3$=H or $C_{1-3}$alkyl;
E=O or $H_2$;
$R_4$=H or $CH_3$;
Q=piperdinyl, pyrrolidinyl, $C_{3-8}$ cycloalkyl, phenyl, substituted phenyl, naphthyl, pyridyl, or is absent;
G=N, CH, or is H;
$R^5$=H or $C_{1-3}$ alkyl, or is absent if G is H;
$R_6$=H or $CH_3$;
W=H, arylacyl, heteroarylacyl, aryl$C_{1-3}$alkylsulfonyl, arylsulfonyl, substituted arylsulfonyl, aryl$C_{1-4}$alkenylsulfonyl, $C_{1-8}$alkylsulfonyl, heteroaryl$C_{1-3}$alkylsulfonyl, heteroarylsulfonyl, aryloxycarbonyl, $C_{1-6}$ alkyloxycarbonyl, aryl$C_{1-3}$alkyloxycarbonyl, arylaminocarbonyl, $C_{1-6}$-alkylaminocarbonyl, aryl$C_{1-3}$ alkylaminocarbonyl, HOOCC-$C_{0-3}$alkylcarbonyl, or is absent if G is H;
X=H, $C_{1-3}$alkyl, NR'R", NH—C(NR'R")=NH, NH—C(NHR')=NR", S—C(NR'R")=NH, S—C(NHR')=NR", C(NR'R")=NH, C(NHR')=NR", or CR'=NR"; where: R',R" are the same or different and =H. $C_{1-6}$alkyl, $C_{1-3}$arylalkyl, aryl or where R'R" forms a cyclic ring containing $(CH_2)_p$ where p=2–5, with the proviso that when X is H or $C_{1-3}$alkyl, then A must contain at least one N atom;
Z=H, $C_{1-3}$alkyl, NR'NR", NH—C(NR'R")NH, NH—C(NHR')=NR", S—C(NR'R")=NH, S—C(NHR')=NR", C(NR'R")=NH, C(NHR')=NR", or CR'=NR"; where: R',R" are the same or different and =H, $C_{1-6}$alkyl, $C_{1-3}$arylalkyl, aryl or where R'R" forms a cyclic ring containing $(CH_2)p$ where p=2–5, with the proviso that when Z is H or $C_{1-3}$alkyl, then Q must contain at least one N atom;

and all pharmaceutically acceptable isomers, salts, hydrates, solvates and prodrug derivatives thereof.

2. The compound of claim 1, having the formula:.

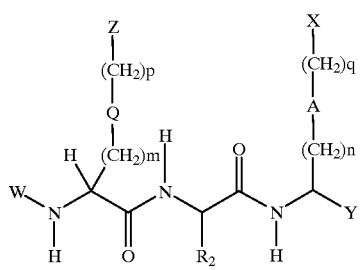

wherein:
m=0,1,2,3,4;
n=0,1,2,3,4;
p=0,1,2,3,4;
q=0,1,2,3,4;
Y=CHO, $COCF_3$, $COCF_2CF_3$, $COCO_2R_7$, $COCONR_8R_9$; where: $R_7,R_8,R_9$ are the same or different and =H, $C_{1-6}$alkyl, $C_{3-8}$cycloalkyl, aryl$C_{1-3}$alkyl, heteroaryl$C_{1-3}$alkyl;
A=piperdinyl, pyrrolidinyl, cyclopropyl, cyclobutyl, cylopentyl, cyclohexyl, phenyl, $C_{3-6}$heteroaryl or is absent;
$R_2$=H or $C_{1-3}$aikyl;
Q=piperdinyl, pyrrolidinyl,$C_{3-8}$ cycloalkyl, phenyl, substituted phenyl, naphthyl, pyridyl, or is absent;
W=H, arylacyl, heteroarylacyl, aryl$_{1-3}$alkylsulfonyl, arylsulfonyl, substituted arylsulfonyl, aryl$C_{1-4}$alkenylsulfonyl, $C_{1-8}$ alkylsulfonyl, heteroaryl$C_{1-3}$allkylsulfonyl, heteroarylsulfonyl, aryloxycarbonyl, $C_{1-6}$alkyloxycarbonyl, aryl$C_{1-3}$alkyloxycarbonyl, arylaminocarbonyl, $C_{1-6}$alkylaminocarbonyl, aryl$C_{1-3}$ alkylaminocarbonyl, or HOOC—$C_{0-3}$alkylcarbonyl;
X=H, $C_{1-3}$alkyl, NR'R", NH—C(NR'R")=NH, NH—C(NHR')=NR", S—C(NR'R")=NH, S—C(NHR")=NR", C(NR'R")=NH, C(NHR')=NR", or CR'=NR"; where: R',R" are the same or different and =H, $C_{1-6}$alkyl, $C_{1-3}$arylalkyl, aryl or where R'R" forms a cyclic ring containing $(CH_2)_p$ where p=2–5, with the proviso that when X is H or $C_{1-3}$alkyl, then A must contain at least one N atom;
Z=H, $C_{1-3}$alkyl, NR'R", NH—C(NR'R")=NH, NH—C(NHR')=NR", S—C(NR'R")=NH, S—C(NHR')=NR", C(NR'R")=NH, C(NHR')=NR", or CR'=NR"; where: R',R" are the same or different and =H, $C_{1-6}$alkyl, $C_{1-3}$arylalkyl, aryl or where R'R" forms a cyclic ring containing $(CH_2)_p$ where p=2–5, with the proviso that when Z is H or $C_{1-3}$alkyl, then Q must contain at least one N atom;

and all pharmaceutically acceptable isomers, salts, hydrates, solvates and prodrug derivatives thereof.

3. The compound of claim 1, having an IC$_{50}$ for Factor Xa of less than about 200 nM.

4. The compound of claim 1, having an IC$_{50}$ for prothrombinase of less than about 2.0 µM.

5. The compound of claim 1, having an IC$_{50}$ for thrombin of greater than about 1.0 µm.

6. A compound selected from a group consisting of:

H-D-Arg-Gly-Arg-H
Boc-D-Arg-Gly-Arg-H
HOOCCO-D-Arg-Gly-Arg-H
HOOCCH$_2$CO-D-Arg-Gly-Arg-H
HOOC(CH$_2$)$_2$CO-D-Arg-Gly-Arg-H
PhCH$_2$CH$_2$CO-D-Arg-Gly-Arg-H
PhCH$_2$SO$_2$-D-Arg-Gly-Arg-H
EtOCO-D-Arg-Gly-Arg-H
2-NaphthoxyAc-D-Arg-Gly-Arg-H
Boc-D-Cit-Gly-Arg-H
Boc-D-Lys-Gly-Arg-H
Boc-D-Har-Gly-Arg-H
Boc-D-Har((CH$_3$)$_4$)Gly-Arg-H
Boc-D-Arg-Ala-Arg-H
Boc-D-Arg-D-Ala-Arg-H
Boc-D-Arg-β-Ala-Arg-H
Boc-D-Arg-Aib-Arg-H
Boc-D-(2,3-Dap)-Gly-Arg-H
Boc-D-(2,4-Dab)-Gly-Arg-H
γ-Abu-Gly-Arg-H
Boc-D-Orn-Gly-Arg-H
Boc-D-homoLys-Gly-Arg-H
Boc-Bag-Gly-Arg-H
Boc-D-4-Gpa-Gly-Arg-H
Boc-D-3Gpa-Gly-Arg-H
Boc-D-4-Apa-Gly-Arg-H
Boc-D-3Apa-Gly-Arg-H
Boc-D-4-Acg-Gly-Arg-H
Boc-D(4NH$_2$Phe)-Gly-Arg-H
Boc-D-(3NH$_2$Phe)-Gly-Arg-H
BnSO$_2$-D-(2,3-Dap)-Gly-Arg-H
BnSO$_2$-D-(2,4-Dab)-Gly-Arg-H
BnSO$_2$-D-Orn-Gly-Arg-H
BnSO$_2$-D-homoLys-Gly-Arg-H
BnSO$_2$-Bag-Gly-Arg-H
BnSO$_2$-D-4-Gpa-Gly-Arg-H
BnSO$_2$-D-3-Gpa-Gly-Arg-H
BnSO$_2$-D-4-Apa-Gly-Arg-H
BnSO$_2$-D-3-Apa-Gly-Arg-H
BnSO$_2$-D-4-Acg-Gly-Arg-H
BnSO$_2$-D-(4-NH$_2$Phe)-Gly-Arg-H
BnSO$_2$-D(3NH$_2$Phe)-Gly-Arg-H
BnSO$_2$-D-(2,3-Dap)-Gly-Arg-CONH$_2$
BnSO$_2$-D-(2,4-Dab)-Gly-Arg-CONH$_2$
BnSO$_2$-D-Orn-Gly-Arg-CONH$_2$
BnSO$_2$-D-homoLys-Gly-Arg-CONH$_2$
BnSO$_2$-Bag-Gly-Arg-CONH$_2$
BnSO$_2$-D-4-Gpa-Gly-Arg-CONH$_2$
BnSO$_2$-D-3-Gpa-Gly-Arg-CONH$_2$
BnSO$_2$-D-4-Apa-Gly-Arg-CONH$_2$
BnSO$_2$-D-3-Apa-Gly-Arg-CONH$_2$
BnSO$_2$-D-4Acg-Gly-Arg-CONH$_2$
BnSO$_2$-D-(4-NH$_2$Phe)-Gly-Arg-CONH$_2$
BnSO$_2$-D-(3-NH$_2$Phe)-Gly-Arg-CONH$_2$
BnSO$_2$-D-Arg-Gly-(2,4Dab)-H
BnSO$_2$-D-Arg-Gly-(homoLys)-H
BnSO$_2$-D-Arg-Gly-(4Gpa)-H
BnSO$_2$-D-Arg-Gly-(3-Gpa)-H
BnSO$_2$-D-Arg-Gly-(4Apa)-H
BnSO$_2$-D-Arg-Gly-(3-Apa)-H
BnSO$_2$-D-Arg-Gly-(4-Acg)-H
BnSO$_2$-D-Arg-Gly-(4NH$_2$Phe)-H
BnSO$_2$-D-Arg-Gly-(3-NH$_2$Phe)-H
Boc-D-Arg-Gly-Arg-CONHEtPh
Boc-D-3-PIA-Gly-Arg-CONHEtPh
Boc-D-4-PIA-Gly-Arg-CONHEtPh
Boc-D-3-GPIA-Gly-Arg-CONHEtPh
Boc-D-4-GPIA-Gly-Arg-CONHEtPh
Boc-D-3-PIG-Gly-Arg-CONHEtPh
Boc-D-4-PIG-Gly-Arg-CONHEtPh
Boc-D-3-GPIG-Gly-Arg-CONHEtPh
Boc-D-4-GPIG-Gly-Arg-CONHEtPh
BnSO$_2$-D-Arg-Gly-Arg-CONHEtPh
BnSO$_2$-D-3-PIA-Gly-Arg-CONHEtPh
BnSO$_2$-D-4-PIA-Gly-Arg-CONHEtPh
BnSO$_2$-D-3-GPIA-Gly-Arg-CONHEtPh
BnSO$_2$-D-4-GPIA-Gly-Arg-CONHEtPh
BnSO$_2$-D-3-PIG-Gly-Arg-CONHEtPh
BnSO$_2$-D-4-PIG-Gly-Arg-CONHEtPh
BnSO$_2$-D-3-GPIG-Gly-Arg-CONHEtPh
BnSO$_2$-D-4-GPIG-Gly-Arg-CONHEtPh
D-Arg-Gly-Arg-CONHEtPh
D-3-PIA-Gly-Arg-CONHEtPh
D-4-PIA-Gly-Arg-CONHEtPh
D-3-GPIA-Gly-Arg-CONHEtPh
D-4-GPIA-Gly-Arg-CONHEtPh
D-3-PIG-Gly-Arg-CONHEtPh
D4-PIG-Gly-Arg-CONHEtPh
D-3-GPIG-Gly-Arg-CONHEtPh
D-4-GPIG-Gly-Arg-CONHEtPh
BnSO$_2$-D-Arg-Gly-Arg-CON(CH$_2$)$_4$
BnSO$_2$-D-3-PIA-Gly-Arg-CON(CH$_2$)$_4$
BnSO$_2$-D-4-PIA-Gly-Arg-CON(CH$_2$)$_4$
BnSO$_2$-D-3-GPIA-Gly-Arg-CON(CH$_2$)$_4$
BnSO$_2$-D-4-GPIA-Gly-Arg-CON(CH$_2$)$_4$
BnSO$_2$-D-3-PIG-Gly-Arg-CON(CH$_2$)$_4$
BnSO$_2$-D-4-PIG-Gly-Arg-CON(CH$_2$)$_4$
BnSO$_2$-D-3-GPIG-Gly-Arg-CON(CH$_2$)$_4$
BnSO$_2$-D-4-GPIG-Gly-Arg-CON(CH$_2$)$_4$
Boc-D-Arg-Gly-Arg-CONHBn Boc-D-3-PIA-Gly-Arg-CONHBn
Boc-D-4-PIA-Gly-Arg-CONHBn
Boc-D-3GPIA-Gly-Arg-CONHBn
Boc-D-4-GPIA-Gly-Arg-CONHBn
Boc-D-3-PIG-Gly-Arg-CONHBn
Boc-D-4-PIG-Gly-Arg-CONHBn
Boc-D-3-GPIG-Gly-Arg-CONHBn
Boc-D-4-GPIG-Gly-Arg-CONHBn
Boc-D-Arg-Gly-Arg-CONHCH$_3$
Boc-D-3-PIA-Gly-Arg-CONHCH$_3$
Boc-D-4-PIA-Gly-Arg-CONHCH$_3$
Boc-D-3-GPIA-Gly-Arg-CONHCH$_3$
Boc-D-4-GPIA-Gly-Arg-CONHCH$_3$
Boc-D-3-PIG-Gly-Arg-CONHCH$_3$
Boc-D-4-PIG-Gly-Arg-CONHCH$_3$
Boc-D-3-GPIG-Gly-Arg-CONHCH$_3$
Boc-D-4-GPlG-Gly-Arg-CONHCH3
D-Arg-Gly-Arg-CONHPh
Boc-D-3-PIA-Gly-Arg-CONHPh
Boc-D-4-PIA-Gly-Arg-CONHPh
Boc-D-3-GPIA-Gly-Arg-CONHPh
Boc-D-4-GPIA-Gly-Arg-CONHPh
Boc-D-3-PIG-Gly-Arg-CONHPh
Boc-D-4-PIG-Gly-Arg-CONHPh
Boc-D-3-GPlG-Gly-Arg-CONHPh
Boc-D-4-GPIG-Gly-Arg-CONHPh
BnSO$_2$-D-Arg-Gly-Arg-CONBn
BnSO$_2$-D-3-PIA-Gly-Arg-CONBn
BnSO$_2$-D-4-PIA-Gly-Arg-CONBn
BnSO$_2$-D-3-GPIA-Gly-Arg-CONBn
BnSO$_2$-D-4-GPIA-Gly-Arg-CONBn
BnSO$_2$-D-PIG-Gly-Arg-CONBn
BnSO$_2$-D-4-PIG-Gly-Arg-CONBn
BnSO$_2$-D-3-GPIG-Gly-Arg-CONBn
BnSO$_2$-D-GPIG-Gly-Arg-CONBn.

7. A pharmaceutical composition treating a thrombosis condition in a mammal, said composition comprising a therapeutically acceptable carrier and a therapeutically effective amount of a compound of claim 1, 2 or 6.

8. A method for treating thrombosis condition in a mammal, said method comprising administering to said mammal a therapeutically effective amount of a compound of claim 1, 2 or 6.

9. A metlhod for inhibiting the coagulation of a blood sample, comprising contacting said sample with a compound of claim 1, 2 or 6 under conditions to effect inhibition of coagulation in said blood sample.

10. The method of claim 8, wherein the condition is selected from the group consisting of:
acute coronary syndrome, myocardial infarction, unstable angina, refractory angina, occlusive coronary thrombus occurring post-thrombolytic therapy or post-coronary angioplasty; a thrombotically mediated cerebrovascular syndrome; embolic stroke; thrombolic stroke, transient ischemic attacks, venous thrombosis,,deep venous thrombosis, pulmonary embolus; coagulopathy, disseminated intravascular coagulation, thrombotic thrombocytopenic purpura, thromboangiitis obliterans, thrombotic disease associated with heparin-induced thrombocytopenia, thrombotic complications associated with extracorporeal circulafton, thrombotic complications associated with instrumentation; and conditions requiring the filting of prosthetic devices.

11. The method of claim 10, wherein said instrumentation is selected from the group consisting of: cardiac catheterization, intravascular catheterization, intra-aortic balloon pump, coronary stent and cardiac valve.

\* \* \* \* \*